(12) United States Patent
Goff et al.

(10) Patent No.: US 6,469,153 B1
(45) Date of Patent: Oct. 22, 2002

(54) EIP-1 AND EIP-3 GENES, ENVELOPE-INTERACTING PROTEINS, EIP-1 AND EIP-3

(75) Inventors: Stephen P. Goff, Tenafly, NJ (US); Xingqiang Li, Chestnut Hill, MA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/082,358

(22) Filed: May 20, 1998

(51) Int. Cl.$^7$ .................. C07H 21/04; C12N 15/00; C12P 21/06
(52) U.S. Cl. .................. 536/23.5; 435/320.1; 435/69.1
(58) Field of Search .................. 435/69.1, 70.1, 435/71.1, 71.2, 252.3, 320.1, 325, 471; 536/23.5

(56) References Cited

PUBLICATIONS

Andreadis, S., and Palsson, B., (1997) Coupled effects of polybrene and calf serum on the efficiency of retroviral transduction and the stability of retroviral vectors. *Human Gene Therapy*, 8(3):285–291 (Exhibit 1).
Chen, Y. et al., (1992) HIV–1 gp41 contains two sites for interaction with several proteins on the helper T–lymphoid cell line, H9. *AIDS*, 6(6):533–39 (Exhibit 2).
Delwart, E.L. et al., (1990) Retroviral envelope glyoproteins contain a "leucine zipper" –like repeat. *AIDS Res. Human Retroviruses*, 6(6):703–06 (Exhibit 3).
Deng, H. et al., (1996) Identification of a major co–receptor for primary isolates of HIV–1. *Nature*, 381(6584):661–66 (Exhibit 4).
Dragic, T. et al., (1996) HIV–1 entry into CD4+ cells is mediated by the chemokine receptor CC–CKR–5. *Nature*, 381(6584):667–73 (Exhibit 5).
Ebenbichler, C.F. et al., (1993) Cell surface proteins binding to recombinant soluble HIV–1 and HIV–2 transmembrane proteins. *AIDS*, 7(4):489–95 (Exhibit 6).
Ebenbichler, C.F. et al., (1996) The human immunodeficency virus type 1 transmembrane gp41 protein is a calcium–binding protein and interacts with the putative second–receptor molecules in a calcium–dependent manner. *J. Virology*, 70(3):1723–28 (Exhibit 7).
Fass, D. et al., (1996) Retrovirus envelope domain at 1.7 Å resolution. *Nature Strutural Biology*, 3(5):465–69 (Exhibit 8).
Feng, Y. et al., (1996) HIV–1 cofactor: Functional cDNA cloning of a seven–transmembrane, G protein–coupled receptor. *Science*, 272(5263):872–77 (Exhibit 9).

Hopkins, N., (1993) High titers of retrovirus (vesicluar stomatitis virus) pseudotypes, at last. *Proc. Natl. Acad. Sci. USA*, 90(19):8759–60 (Exhibit 10).
Lam, J.S. et al., (1996) Improved gene transfer into human lymphocytes using retroviruses with the Gibbon Ape leukemia virus envelope. *Human Gene Therapy*, 7(12):1415–22 (Exhibit 11).
Li, X. et al., (1996) Homomeric interaction between transmembrane proteins of moloney murine leukemia virus. *J. Virology*, 70(2):1266–70 (Exhibit 12).
Lu, M. et al., (1995) A trimeric structural domain of the HIV–1 transmembrane glycoprotein. *Nature Structural Biology*, 2(12):1075–82 (Exhibit 13).
Ory, D.S. et al., (1996) A stable human–derived packaging cell line for production of high titer retrovirus/vesicular stomatitis virus G pseudotypes. *Proc. Natl. Acad. Sci. USA*, 93(21):11400–06 (Exhibit 14).
Porter, C.D. et al., (1996) Comparison efficiency of infection of human gene therapy target cells via four different retroviral receptors. *Human Gene Therapy*, 7(8):913–19 (Exhibit 15).
Singh, D., and Rigby, P., (1996) The use of histone as a facilitator to improve the efficiency of retroviral gene transfer. *Nucleic Acids Res.*, 24(15):3113–14 (Exhibit 16).

*Primary Examiner*—Gary L. Kunz
*Assistant Examiner*—Robert S. Landsman
(74) *Attorney, Agent, or Firm*—John P. White; Cooper & Dunham LLP

(57) ABSTRACT

This invention provides isolated nucleic acid molecules encoding envelope-interacting protein-1 and envelope-interacting protein-3. This invention provides fusion proteins comprising EIP-1, EIP-3, or fragments thereof and a second peptide. This invention provides vectors comprising the isolated nucleic acid molecule, encoding mammalian EIP-1 and EIP-3. This invention provides plasmid designated pCGN-EIP-l and pCGN-EIP-3. This invention provides purified mammalian EIP-1 and EIP-3 proteins. This invention provides monoclonal or polyclonal antibodies directed to epitopes of an EIP-1 or an EIP-3. This invention provides a method of increasing transduction efficieny of a retrovirus on target cells comprising: a) incubating an envelope-interacting protein with a retrovirus; and b) transducing the target cells with the retrovirus. This invention provide methods of treating patient with a therapeutic gene comprising use of transducing viruses incubated with an effective amount of an envelope-interacting protein effective to enhance retroviral infectivity. This invention also provides pharmaceutical composition comprising an envelope-interacting protein bound retroviral virion comprising a therapeutic gene and a pharmaceutically acceptable carrier capable of passing through a cell membrane.

24 Claims, 16 Drawing Sheets

*FIGURE 2A*

```
1/1
GAG GTA CCG ACC CTT GAC GTC GGG GTA CTA CCT CAT CCC TCG GGC GTG ATG GCT ACG GGC
glu val pro thr leu asp val gly val leu pro his pro ser gly val met ala thr gly
 arg tyr arg pro leu thr ser gly tyr tyr leu ile pro arg ala OPA trp leu arg ala
  gly thr asp pro OPA arg arg gly thr thr ser ser leu gly arg asp gly tyr gly arg
61/21                                    91/31
GCA GAT GTA CGA GAC ATT CTA GAA CTC GGG GGT CCA GAG GGA GAT GCC GCC TCT GGG ACC
ala asp val arg asp ile leu glu leu gly gly pro glu gly asp ala ala ser gly thr
 gln met tyr glu thr phe AMB asn ser gly val gln arg glu met pro pro leu gly pro
  arg cys thr arg his ser arg thr arg gly ser arg gly arg cys arg leu trp asp his
121/41                                   151/51
ATC AGC AAA AAG GAT ATT ATC AAC CCG GAC AAG AAA AAG TCC AAG AAG TCC TCA GAG ACG
ile ser lys lys asp ile ile asn pro asp lys lys lys ser lys lys ser ser glu thr
 ser ala lys arg ile leu ser thr arg thr arg lys ser pro arg ser pro gln arg arg
  gln gln lys gly tyr tyr gln pro gly gln glu lys val gln glu val leu arg asp ala
181/61                                   211/71
CTG ACC TTC AAG AGG CCT GAG GGC ATG CAT CGG GAG GTC TAT GCT TTG CTT TAC TCT GAC
leu thr phe lys arg pro glu gly met his arg glu val tyr ala leu leu tyr ser asp
 OPA pro ser arg gly leu arg ala cys ile gly arg ser met leu cys phe thr leu thr
  asp leu gln glu ala OPA gly his ala ser gly gly leu cys phe ala leu leu OPA gln
241/81                                   271/91
AAA AAG GAT GCA CCC CCA CTG CTG CCC AGT GAC ACT GGT CGG GGG CAT CGG ACA GTG AAG
lys lys asp ala pro pro leu leu pro ser asp thr gly arg gly his arg thr val lys
 lys arg met his pro his cys cys pro val thr leu val gly gly ile gly gln OPA arg
  lys gly cys thr pro thr ala ala gln OPA his trp ser gly ala ser asp ser glu gly
```

FIGURE 2B

301/101
GCG AAA CTG GGG TCC AAG AAG GTT CGC CCT TGG AAA TGG ATG CCT TTT ACT AAC CCA GCT
ala lys leu gly ser lys lys val arg pro trp lys trp met pro phe thr asn pro ala 331/111
arg asn trp gly pro arg arg phe ala leu gly asn gly cys leu leu leu thr gln leu
glu thr gly val gln gln gly ser pro leu gly met asp ala phe tyr OCH pro ser ser 361/121
CGA AAG GAC GGC GCT ATG TTT TTC CAC TGG CGA CGA GCG GCG GAG GAG AAG GAC TAC
arg lys asp gly ala met phe phe his trp arg arg ala ala glu glu gly lys asp tyr
glu arg thr ala leu cys phe ser thr gly asp glu arg arg arg ala arg thr thr 391/131
lys gly arg arg tyr val phe pro leu ala thr ser gly gly gly gly gln gly leu pro 421/141
CCT TTT GCC AGG TTC AAT AAG ACG GTG CAG GTG CCC GTG TAC TCA GAG CAG TAC CAA
pro phe ala arg phe asn lys thr val gln val pro val tyr ser glu gln glu tyr gln
leu leu pro gly ser ile arg arg cys arg cys pro cys thr gln ser arg ser thr asn 451/151
phe cys gln val gln OCH asp gly ala gly ala arg val leu arg ala gly val pro thr 481/161
CTC TAC CTT CAT GAT GAC GCA TGG GAC GAG ACT GAC GCA GAG ACT GAC CAC TTT GAC CTC AGC
leu tyr leu his asp asp ala trp asp thr lys ala glu thr asp his leu phe asp leu ser
ser thr phe met met thr his gly leu arg leu thr thr tyr leu thr ser ala 511/171
leu pro ser OPA OPA arg met asp OCH gly arg asp OPA pro pro ile OPA pro gln pro 541/181
CGC CGA TTT GAT CTG CGC TTC GTA GTT ATT CAC GAT CGG TAT GAC CAG CAG TTC AAG
arg arg phe asp leu arg phe val val ile his asp arg tyr asp his gln gln phe lys
ala asp leu ile cys ala ser AMB leu phe thr ile gly met thr thr ser ser arg 571/191
pro ile OPA ser ala leu arg ser tyr ser arg ser val OPA pro pro ala val gln glu 601/201
AAG CGT TCT GTG GAG GAC CTG AAA GAG AGG TAC TAC CAC ATT TGT GCC AAG CTT GCC AAC
lys arg ser val glu asp leu lys glu arg tyr tyr his ile cys ala lys leu ala asn
ser val leu trp arg thr OPA lys arg gly thr thr phe val pro ser leu pro thr 631/211
ala phe cys gly gly pro gly arg glu val leu pro his leu cys gln ala cys gln arg 661/221
GTG AGG GCT GTG CCA GGC ACA GAT CTC AAG ATA CCA GTG TTT GAT GCT GGG CAT GAG AGA
val arg ala val pro gly thr asp leu lys ile pro val phe asp ala gly his glu arg
OPA gly leu cys gln ala gln ile ser arg tyr gln cys leu met gly met arg asp 691/231
glu gly cys ala arg his arg ser gln asp thr ser val OPA cys trp ala OPA glu thr

FIGURE 2C

```
721/241
CGG CGG AAG GAA CAG CTA GAG CGG CTT TAC AAC CGA ACC CCA GAG CAG GTG GCA GAG GAG
arg arg lys glu gln leu glu arg leu tyr asn arg thr pro glu gln val ala glu glu
                                      751/251
gly gly arg asn ser AMB ser gly phe thr glu pro gln ser arg pro gln arg arg
    ala glu gly thr ala arg ala ala leu gln pro asn pro arg ala gly gly arg gly gly
781/261                                                              811/271
GAG TAC CTC CTA CAG GAG CTG CGT AAG ATT GAG GCC CGG AAA AAA GAG CGG GAG AAG CGC
glu tyr leu leu gln glu leu arg lys ile glu ala arg lys lys glu arg glu lys arg
ser thr ser tyr arg ser cys val arg leu arg pro gly lys lys ser gly arg ser ala
    val pro pro thr gly ala ala OCH asp OPA gly pro gly lys arg ala gly glu ala gln
841/281                                                              871/291
AGC CAA GAC CTG CAG AAG CTG ATT ACA GCA GCA GAC ACT GCA GAG CAG CGG CGC ACG
ser gln asp leu gln lys leu ile thr ala ala asp thr ala glu gln arg arg thr
ala lys thr cys arg ser OPA leu gln gln thr pro leu gln ser ser gly ala arg
    pro arg pro ala glu ala asp tyr ser ser arg his his cys arg ala ala ala his gly
901/311                                         931/311
GAA CGC AAG GCT CCC AAG AAG AAG CTA CCC CAA AAG AAG GAG GCT GAG AAG CCG GCT GTC
glu arg lys ala pro lys lys lys leu pro gln lys lys glu ala gly lys pro ala val
asn ala arg leu pro arg arg ser tyr pro lys arg arg arg leu arg ser arg leu ser
    thr gln gly ser gln glu gly ala thr pro lys gly gly gly OPA glu ala gly cys pro
961/321                                         991/331
CCT GAG ACT GCA GGC ATC AAG TTT CCA GAT TTT AAG TCG GCA GGT GTC ACG CGG AGC
pro glu thr ala gly ile lys phe pro asp phe lys ser ala gly val thr leu arg ser
leu arg leu gln ala ser ser phe gln ile leu leu ser arg gln val ser arg tyr gly ala
    OPA asp cys arg his gln val ser arg phe OCH val gly arg cys his ala thr glu pro
1021/341                                        1051/351
CAG CGG ATG AAG CTA AAG CTA CCC AGC TCT GTG GGT CAG AAG AAG ATC AAG GCG CTG ATG
gln arg met lys leu lys leu pro ser ser val gly gln lys lys ile lys ala leu gln met
ser gly OPA ser tyr pro ala leu trp val arg arg arg arg ser arg arg trp asn arg cys
    ala asp glu ala thr gln leu cys gly ser gly glu asp gln gly ala gly thr asp ala
1081/361                                        1111/371
CTG CTG GAA CTT GGT GTG GAG CTG AGC CCT ACC CCC ACA GAG GAG CTG GTG CAT ATG TTC
leu leu glu leu gly val glu leu ser pro thr pro thr glu leu val his met phe
cys trp asn leu val trp ser OPA ala leu pro pro gln arg ser trp cys ile cys ser
    ala gly thr trp cys gly ala glu pro tyr pro his arg gly ala gly ala tyr val gln
```

FIG. 2D

1141/381
AAT GAG TTG CGG AGC GAC CTG GTG TTA CTT TAC GAG CTC AAG CAG GCC TGT GCC AAC TGT
asn glu leu arg ser asp leu val leu tyr glu leu lys gln ala cys ala asn cys
                                            1171/391
met ser cys gly ala thr trp cys tyr phe thr ser ser arg pro val pro thr val
OPA val ala glu arg pro gly val thr leu arg ala gln ala gly leu cys gln leu OPA
1201/401
GAA TAT GAG CTA CAG ATG CTG CGG CAC CGG CAG GCC CTG GCT CGG GCA GGA GTG CTG
glu tyr glu leu gln met leu arg his arg his gln ala leu ala arg ala gly val leu
                            1231/411
asn met ser tyr arg cys gly thr gly thr arg pro leu gly gln glu cys trp
ile OPA ala thr asp ala ala ala pro ala arg gly pro gly ser gly arg ser ala gly
1261/421                                    1291/431
GGG GCC CCT GCC GCA GCA GCA GTG GGA CCA ACC CCG GCT TCT GCT GAG CCA ACA GTG TCT
gly ala pro ala ala ala val gly pro thr pro ala ser ala glu pro thr val ser
gly pro leu pro gln gln gln trp asp gln pro arg leu leu leu ser gln leu cys leu
1321/441                        1351/451
gly pro cys arg ser ser gly thr asn pro gly phe cys OPA ala asn ser val OPA
GAA TCT GGA CTT GGT CTG GAC CCC AAG GAT ACC ATC ATT GAT GTC GTG GGT GCA CCC
glu ser gly leu gly leu asp pro thr lys asp thr ile ile asp val val gly ala pro
                    1381/461
asn leu asp leu val trp thr pro pro arg ile pro ser leu met ser trp val his pro
ile trp thr trp ser gly pro his gln gly tyr his OPA cys arg gly cys thr pro
CTC ACA CCC AAT TCG CGG AAA CGA CGG GAA TCA GCC TCC AGC TCA TCT TCT GTG AAG AAA
leu thr pro asn ser arg lys arg arg glu ser ala ser ser ser ser val lys lys
                1411/471
ser his pro ile arg gly asn asp gly asn gln pro pro ala his leu leu OPA arg lys
                        1441/481                                1471/491
his thr gln phe ala glu thr thr gly ile ser leu gln leu ile phe cys glu glu ser
GCC AAG AAA CCA TAA GGG GCC ATC TGA GTT GGT GGT ATG GTG TAA ATA GAG CTG TTA CAT
ala lys lys pro OCH gly ala ile OPA val gly gly met val OCH ile glu leu leu his
pro arg asn his lys gly pro ser glu leu val val trp cys lys AMB ser cys tyr ile
                                    1501/501
gln glu thr ile arg gly his leu ser trp trp tyr gly val asn arg ala val thr leu
1501/511
TGA AAA AAA AAA AAA AAA AAA AAA AAA AAA AAA AAA CTC GAC
OPA lys lys lys lys lys lys lys lys lys lys lys lys leu asp
glu lys lys lys lys lys lys lys lys lys lys lys lys asn ser
lys lys lys lys lys lys lys lys lys lys lys lys thr arg

FIGURE 3A

```
1/1
CGG AAC TGG TCG GGA TGA GTG GCG GAG GCA CCG AGA CCC CTG TAG CGT GCG ACG CCG CCC
arg asn trp ser gly OPA val ala glu ala pro arg pro leu AMB arg ala thr pro pro
                            31/11
GGG ACG GCG AGA AGC GGG ACT CAC TGG GGA CTC CGG GTG CGG CGC ACC TCA TTA TCA AGG
gly thr gly arg asp glu trp arg arg his arg asp pro cys ser val arg arg arg pro
glu leu val gly met ser gly gly thr glu thr pro val ala cys asp ala ala gln
61/21
AGG GCG GCA AGA AGC GGG ACT CAC TGG GGA CTC CGG GTG CGG CGC ACC TCA TTA TCA AGG
arg ala ala arg ser gly thr his trp gly leu arg val arg arg ser leu ser arg
                                                                          91/31
gly arg gln glu ala gly leu thr gly leu asp ser gly cys gly ala pro his tyr gln gly
gly gly lys lys arg asp ser leu gly thr pro gly ala ala his leu ile ile lys asp
121/41                                         151/51
ATC TTG GAG AGA TTC ATT CCA GGC TGC TGG ATC ACA GAC CAG TTA CCC AAG GTG AAA TCC
ile leu glu arg phe ile pro gly cys trp ile thr asp gln leu pro lys val lys ser
ser trp arg asp ser phe gln ala ala gly ser gln thr ser tyr pro arg OPA asn pro
                                                                         211/71
leu gly glu ile his ser arg leu leu asp his arg pro val thr gln gly ile arg
181/61
GTT ACT TTG TAA AAG AAT TTG AAG AAA AAC GTG GCC TTC GAG AAT TGC GCG TTC TTA AGA
val thr leu OCH lys asn leu lys lys asn val ala phe glu asn cys ala phe leu arg
leu leu cys lys arg ile OPA arg lys glu thr trp pro ser arg ile ala arg ser OCH glu
                                                                         271/91
tyr phe val lys glu phe gln glu lys arg gly leu arg glu val leu arg val lys asn
241/81
ACT TGG AGA ATA CGA TCC AGG AAA CAA ATG AGT GCC TGC TTC CCA AAT GCA GAG AGA CCA
thr trp arg ile arg ser arg lys gln met ser ala cys phe pro asn ala glu arg pro
leu gly glu tyr asp pro gly asn lys OPA val pro ala ser gln met gln arg asp his
leu glu asn thr ile gln glu thr ile arg glu cys leu leu pro lys cys arg glu thr met
```

FIGURE 3B

```
301/101
TGG AGT GCG GCC TGG GGG AGA CCC TGC AGA GAT TGC AAG CAG CTA ACG ACT CCA TCT GCA
trp ser ala ala trp gly arg pro cys arg asp cys lys gln leu thr thr pro ser ala
                              331/111
gly val arg pro gly gly asp pro ala glu ile ala ser ser OCH arg leu his leu gln
glu cys gly leu gly glu thr leu gln arg leu gln ala ala asn asp ser ile cys arg
361/121
GAC TCC AGC AGA GAG AAC AGG AAC GGA AAA AGG TGA TTA ATG ACT ACT TGA CAG CTA GTG
asp ser ser arg arg glu asn arg asn gly lys arg OPA leu met thr thr OPA gln leu val
                              391/131
thr pro ala glu arg thr gly thr glu lys gly asp OCH OPA leu leu asp ser AMB OPA
leu gln gln arg glu gln glu arg lys lys val ile asn asp tyr leu thr ala ser glu
421/141                       451/151
AGA AGC GTC GTC TGC TCC AGT GGG AGG AGT TCG TGA GCG GAC AGC CGC AGC GCA GAG CTG
arg ser val val trp ser ser gly arg ser ser OPA ala asp ser arg ser ala glu leu
glu ala ser ser gly pro val gly gly val arg glu arg thr ala ala ala gln ser OPA
lys arg arg leu val gln trp glu glu phe val ser gly gln pro gln arg arg ala glu
481/161                       511/171
AGG TGG ACG AGG AGC ACA GAA GAG CCG TGG AGA GGC TCC GAG AGC AGT ATG CAG CAA TGG
arg trp thr arg ser thr glu glu pro trp arg gly ser glu ser met gln gln trp
gly gly arg gly ala gln lys ser arg gly gly ala pro arg ala val cys ser asn gly
val asp glu his arg arg ala val glu arg leu arg glu gln tyr ala ala met glu
541/181                       571/191
AGA AGG ACC TGG CCA AGT TTT CCA CCT TTT AAG ACT TTG ATC TAA AAG AGA CAG ATG AAT
arg arg thr trp pro ser phe pro pro phe lys thr leu ile OCH lys arg gln met asn
glu gly pro gly gln val phe his leu leu arg leu leu OPA ser lys arg asp arg OPA met
lys asp leu ala lys phe ser thr phe OCH asp phe asp leu lys glu thr asp glu OPA
601/201                       631/211
GAG GAA GTG CTT TCT CAT TCC CCC AAT CCT CCC ACC AAC CAT GTA GTC TCT CCT TCA AGC
glu glu val leu ser his ser pro asn pro pro thr asn his val val ser pro ser ser
arg lys cys phe leu ile pro pro ile leu pro pro thr met AMB ser leu leu gln ala
gly ser ala phe ser phe pro gln ser ser his gln pro cys ser leu ser phe lys leu
661/221                       691/231
TTA GCA GTA CAC TCA GGT GCA CTC TTA GGT CTG AAG AGA GAC ACT GCC GGA GCC AGA TAC
leu ala val his ser gly ala leu leu gly leu lys arg asp thr ala gly ala arg tyr
AMB gln tyr thr gln gly his ser AMB val OPA arg glu thr leu pro glu pro asp thr
ser ser thr leu arg gly thr leu arg ser gly arg ser gly arg his cys arg gln ile his
```

FIGURE 3C

721/241
ATG TCC AGT GGA AGA AGC GTG CTT CTG CAC CTA ACT GTG GTC ATC TGA AGG AGA GGA GGG
met ser ser gly arg ser val leu his leu thr val val ile OPA arg arg gly gly
          751/251
CYS PRO VAL GLU GLY ALA CYS PHE CYS THR OCH LEU TRP SER SER GLU GLY GLU GLY GLY
cys pro val glu gly ala cys phe cys thr OCH leu trp ser ser glu gly glu gly gly
781/261
VAL GLN TRP LYS LYS ARG ALA SER ALA PRO ASN CYS GLY HIS LEU LYS GLU ARG ARG ALA
val gln trp lys lys arg ala ser ala pro asn cys gly his leu lys glu arg arg ala
                    811/271
CGG TGG GGC ACA TTT GCT GCT GGA CAG ATT TGA TCT TTT CAT TGA TTA GCT TAG AGG GCT
arg trp gly thr phe ala ala gly gln ile OPA ser phe his OPA leu ala AMB arg ala
GLY GLY ALA HIS LEU LEU ASP ARG ASP ARG PHE ASP LEU PHE ILE ASP AMB LEU ARG GLY LEU
gly gly ala his leu leu asp arg asp arg phe asp leu phe ile asp AMB leu arg gly leu
VAL GLY HIS ILE CYS CYS TRP THR ASP LEU ILE PHE SER LEU ILE SER LEU GLU GLY CYS
val gly his ile cys cys trp thr asp leu ile phe ser leu ile ser leu glu gly cys
841/281
GTG AGT GTA GAT TTC TTC ATT CAT TCC ACC AAG GGC AAA TGT TTG ACC TTG TGG ATT AAA
val ser val asp phe phe ile his ser thr lys gly lys cys leu thr leu trp ile lys
OPA VAL AMB ILE SER SER PHE ILE PRO PRO ARG ALA ASN VAL OPA PRO CYS GLY LEU ASN
OPA val AMB ile ser ser phe ile pro pro arg ala asn val OPA pro cys gly leu asn
GLU CYS ARG PHE LEU HIS SER PHE HIS SER GLN GLY GLN MET PHE ASP LEU VAL ASP OCH MET
glu cys arg phe leu his ser phe his ser gln gly gln met phe asp leu val asp OCH met
901/301                                       931/311
TGG CAG GTA TGA CAA CTT CCC ATC ACA GCA TCC TGT GAC AGA GAT ACC ACA GTG GGC TTT
trp gln val OPA gln leu pro ile thr ala ser cys asp arg asp thr thr val gly phe
GLY ARG TYR ASP ASN PHE SER PRO GLN HIS PRO VAL THR GLU ILE PRO GLN TRP ALA LEU
gly arg tyr asp asn phe ser pro gln his pro val thr glu ile pro gln trp ala leu
ALA GLY MET THR THR SER HIS ILE LEU OPA GLN ARG TYR HIS SER GLY LEU OPA
ala gly met thr thr ser his his ile leu OPA gln arg tyr his ser gly leu OPA
961/321                      991/331
GAA CGC TTG CTT GGA GAC ACC AGG TTT TGC AGT GCA ACA CAG TGC CAT GTC TTT CAC TTT
glu arg leu leu gly asp thr arg phe cys ser ala thr gln cys his val phe his phe
ASN ALA CYS LEU GLU THR PRO GLY PHE ALA VAL GLN HIS HIS SER ALA MET SER PHE THR LEU
asn ala cys leu glu thr pro gly phe ala val gln his his ser ala met ser phe thr leu
THR LEU ALA TRP ARG HIS GLN VAL LEU GLN CYS ASN THR VAL PRO CYS LEU SER LEU CYS
thr leu ala trp arg his gln val leu gln cys asn thr val pro cys leu ser leu cys
1021/341                          1051/351
GTG ACA AGA CAT TAC ATG ACT GGT AGC CTT GTA GCA CTT AAT ATT TTC ATT TTC TAA GCT
val thr arg his tyr met thr gly ser leu val ala leu asn ile phe ile phe OCH ala
OPA GLN ASP ILE THR OPA LEU VAL ALA LEU AMB HIS HIS LEU ILE PHE SER PHE SER LYS LEU
OPA gln asp ile thr OPA leu val ala leu AMB his his leu ile phe ser phe ser lys leu
ASP LYS THR LEU HIS ASP TRP AMB PRO CYS SER THR OCH TYR PHE HIS PHE PHE LEU SER ER TYR
asp lys thr leu his asp trp AMB pro cys ser thr OCH tyr phe his phe his ser tyr
1081/361                              1111/371
ATG CTT AGG AGA AAA ACC AAA ATG TAT TTT GAC TTT TTC CTC AAG GAC CAT CAT CTC
met leu arg arg lys thr lys met tyr phe asp phe phe leu ser lys asp his his leu
CYS LEU GLY GLU LYS PRO LYS CYS ILE LEU THR PHE SER SER PRO ARG THR ILE ILE SER
cys leu gly glu lys pro lys cys ile leu thr phe ser ser pro arg thr ile ile ser
ALA AMB GLU LYS ASN GLN ASN VAL PHE OPA LEU PHE PRO LEU GLN GLY PRO SER SER ARG
ala AMB glu lys asn gln asn val phe OPA leu phe pro leu gln gly pro ser ser arg

FIGURE 3D

```
1141/381                                    1171/391
GCC CAT AGA GCT CAC CTT GCT CTC CGC TCC ATT TCG CTC TGG GCC AGC GCT CCA CGG AAC
ala his arg ala his leu ala leu arg ser ile ser leu trp ala ser ala pro arg asn
    pro ile glu leu thr leu leu ser ala pro phe arg ser gly pro ala leu his gly thr
    pro AMB ser ser pro cys ser pro leu his phe ala leu gly gln arg ser thr glu gln
1201/401                                    1231/411
AGT GTC TGT GCA TGA CTC AGC TGC GCA GTG AGT CGG CAG CAG AGT CTG CCA AGT CCT TCC
ser val cys ala OPA leu ser cys ala val ser arg gln gln ser leu pro ser pro ser
    val ser val his asp ser ala ala gln OPA val gly ser arg val cys gln val leu pro
    cys leu cys met thr gln leu arg ser gly ser ala ala glu

FIGURE 3E

```
1561/521
TAA GGC AGA GAA CCC CTA ACT GTC GTG TTA TCT CAG AAT TCT CAA TGC AGA CAA TTG ACA
OCH gly arg glu pro leu thr val val leu ser gln asn ser gln cys arg gln leu thr
                                 1591/531
lys ala glu asn pro OCH leu ser cys tyr leu arg ile leu asn ala asp asn OPA gln
arg gln arg thr pro asn cys arg val ile ser glu phe ser met gln thr ile asp asn
1621/541                                              1651/551
ATG CGT GCC TGT GTA AAT GTA CGT AAA TGT GCT GAC TGT GAG AGC TTC GTT CTT GGC
met arg ala cys val asn val arg lys cys thr ala asp cys glu ser phe val leu gly
cys val pro val OCH met tyr val asn val arg leu thr val arg ala ser phe leu ala
ala cys leu cys lys cys thr OCH met tyr gly OPA leu OPA glu leu arg ser trp leu
1681/561                                              1711/571
TCA TGC TGA AGT GGG ATT AAA GCT AAT AGA AGA GAT GAA AAA AAA AAA AAA AAA
ser cys OPA ser gly ile lys ala asn arg arg asp glu lys lys lys lys lys lys
his ala glu val gly leu lys leu ile glu glu met lys lys lys lys lys lys lys
met leu lys trp asp OCH ser OCH AMB lys arg OPA lys lys lys lys lys lys
```

*FIGURE 5*

| | Isolation Frequency | Homologous Sequences |
|---|---|---|
| EIP-1 | 5 | Several anonymous cDNA clones |
| EIP-2 | 17 | EST105188 Rattus sp. cDNA 3' end |
| EIP-3 | 1 | Several anonymous cDNA clones |
| EIP-4 | 1 | No homology in genbank |
| EIP-5 | 1 | EST110532 Rattus sp. cDNA 5' end |
| EIP-6 | 1 | Several anonymous cDNA clones |
| EIP-7 | 1 | Clone H11078 |
| EIP-8 | 1 | No homology in genbank |
| EIP-9 | 2 | No homology in genbank |
| EIP-10 | 1 | No homology in genbank |
| EIP-11 | 2 | YY11a01 |

*FIGURE 6*

| Gal4AD \ Gal4BD | TM3 | Laminin | Gal4BD Alone | No DNA |
|---|---|---|---|---|
| EIP-1 | + | – | – | – |
| EIP-2 | + | – | – | – |
| EIP-3 | + | – | – | – |
| EIP-4 | + | – | – | – |
| EIP-5 | + | – | – | – |
| EIP-6 | + | – | – | – |
| EIP-7 | + | – | – | – |
| EIP-8 | + | – | – | – |
| EIP-9 | + | – | – | – |
| EIP-10 | + | – | – | – |
| EIP-11 | + | – | – | – |

EIP-1 AND EIP-3 GENES, ENVELOPE-INTERACTING PROTEINS, EIP-1 AND EIP-3

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Advances in understanding of human diseases at molecular level have led to possibility of treating human diseases by introducing genes into specific cells of patients. Gene therapy offers a great promise for modern medicine (Mulligan 1993) (Anderson 1984). The first step of gene therapy is to transduce specific target cells. There are two basic ways to deliver genes. In ex vivo therapy, cells from certain tissues, such as hematopoietic cells, are removed from patients and are infected with vectors which carry therapeutic genes. Cells expressing the therapeutic genes are then returned into patients. Vectors are directly administrated to patients in in vivo therapy. This approach is especially useful when it is difficult to isolate cells from tissues and to be infected in vitro. Advantages with retroviruses include long-term stability of therapeutic genes because viral genome is inserted into human chromosomes.

To engineer retroviruses for gene therapy, viral genes are deleted from viral genome, and an exogenous gene is inserted instead into viral genome. Plasmids containing a viral genome is introduced into a packaging cell line which provides viral components necessary to make viral particles (Cone and Mulligan 1984; Mann et al. 1983; Miller et al. 1985; Sorge et al. 1984; Watanabe and Temin 1983; Markowitz et al. 1988a; Markowitz et al. 1988b). Virions produced from the packaging cell line are used to transduce target cells. In the first step of viral infection, envelope proteins on retroviruses interact with receptors on target cells, which lead to a series of events resulting in fusion of viral membrane and cellular membrane. Viral core containing viral genomes with exogenous genes thus enters cells. Based on their host range, retrovirus vectors commonly used in human gene therapy are classified as ecotropic or amphotropic. Although ecotropic virus can only infect murine cells, modification of envelope protein, such as inserting a ligand epitope for a specific receptor, will expand or change host range, resulting in infection of human cells expressing that particular receptor (Kasahara et al. 1994). Amphotropic virus can infect both murine and human cells. One problem associated with retrovirus vectors is low transduction efficiency. For example, amphotropic virus has been used to infect hematopoietic cells, and transduction efficiency is low. To circumvent this problem, viruses pseudotyped with envelope proteins from other viruses have been tested. For example, Vesicular stomatitis virus (VSV) G protein and Gibbon ape leukemia virus (GALV) envelope protein have been studied in pseudotyping murine leukemia viruses (Hopkins 1993; Ory et al. 1996; Sharma et al. 1996; Wang et al. 1996) (Lam et al. 1996). In general, however, the titers of those vector stocks are still low, preventing successful clinical application of gene therapy in treating human diseases.

Gene therapy holds great promise in modern medicine. Advances in understanding of genetic bases of human diseases make it possible to treat human diseases by transferring normal genes into specific cells of patients. It has been proposed to use gene therapy to treat any human diseases, genetic and acquired (Anderson 1984; Mulligan 1993). Significant advances have been made to develop protocols to deliver exogenous genes into human cells. Vectors, vehicles used to deliver genes, include retroviruses and other viruses. Retroviral vectors, by far, the most extensively studied among viral vectors offer several advantages over other viral vectors, specially in ex vivo strategy of gene therapy. A retroviral vector can transduce any human cells, and lead to a long-term expression of exogenous gene.

To achieve therapeutic effects with gene therapy technology, vectors which express exogenous genes at a level sufficient to achieve therapeutic effects are required. A great deal of effort has been devoted to identify nucleic acid molecule sequences important for gene expression and to incorporate such nucleic acid molecules in vectors to thereby develop vectors which can express therapeutic genes at high levels (Leboulch et al. 1994; Leboulch et al. 1995; Takekosh et al. 1995). In some instances, regulated expression of the therapeutic genes is required (Cone et al. 1987). Retroviruses, offer an excellent choice to introduce exogenous genes into cells because of their ability to infect any kind of cells. In infected cells, retroviral genomes are inserted into host chromosomes, resulting in a long term expression of exogenous genes.

The second important aspect of gene therapy using a retrovirus as vector is the development of safe packaging cell lines (Cone and Mulligan 1984; Mann et al. 1983; Miller et al. 1985; Sorge et al. 1984; Watanabe and Temin 1983; Markowitz et al. 1988a; Markowitz et al. 1988b). In packaging cells, viral components are made and are able to assemble into viral particles. A vector carrying a therapeutic gene and a retroviral packaging signal is introduced into a packaging cell line and is packaged into viral particles. Retrovirus formed in such a way can be used to transduce target cells. To make safe packaging cell lines, viral proteins, gag and pol are expressed from a plasmid, and the envelope is expressed from another plasmid.

The chance of generating wild type virus through recombination is extremely low (Markowitz et al. 1988a; Markowitz et al. 1988b). Because a viral vector contains only a packaging signal, and does not encode any viral proteins, there is only one round of infection.

To successfully apply retroviral gene therapy in treatment of human diseases, several technical problems have to be solved. One of the difficulties involved is low transduction efficiency of retroviral stocks, which is addressed extensively in this study. Amphotropic retrovirus is widely used in gene therapy because of its ability to infect human cells. In transduction of human lymphocytes using retroviruses with amphotropic envelopes, however, transduction efficiency is relatively low. To improve gene therapy efficiency, different viral envelope proteins have been studied for their application in gene therapy. Gibbon Ape leukemia virus envelope virus envelope, for example, has been used to pseudotype murine leukemia viral vector (Lam et al. 1996). Vesicular stomatitis virus (VSV) G protein is another alternative envelope protein used in gene therapy (Hopkins 1993; Porter et al. 1996; Sharma et al. 1996; Wang et al. 1996). It has been shown that retroviral vectors pseudotyped with G protein can transduce human lymphocytes with much higher efficiency than amphotropic retroviral vectors.

In treating human diseases, sometimes specific targeting of certain cell types is required. Different strategies have been used to modify envelope proteins on vectors. For example, a ligand epitope is inserted into the envelope, which enables virus to infect specific cell type (Kasahara et al. 1994). In general, such modifications result in low infection efficiency.

Polybrene, a chemical compound, is often used to increase viral infectivity of retrovirus. In several cases, instead of boosting transduction efficiency, it actually decreases viral transduction efficiency. For example, plates coated with a fibronectin fragment are often used to isolate human stem cells. Polybrene, however, because of its negative charges, will decrease efficiency of fibronectin. Thus, alternatives are needed for enhancing retroviral infectivity in such circumstances.

Discovery of the Envelope-interacting Proteins (EIPs)

Understanding of the basic mechanism used by retroviruses to enter cells will facilitate application of retroviruses as vectors for gene therapy. Envelope proteins of retroviruses including Mo-MLV contain two subunits: the surface protein (SU) and the transmembrane protein (TM). SU mediates binding of the virus to host cells by interacting with specific viral receptors on a host cell surface, which triggers a complex process leading to fusion of viral and cellular membranes mediated by TM (Hunter and Swanstrom 1990; Marsh and Helenius 1989). These early events of viral infection are poorly understood. Several lines of evidence suggest that host factors are involved in these early events of viral infection. Recently the second receptors for human immunodeficiency virus (HIV) have been identified and cloned (Deng et al. 1996; Dragic et al. 1996; Feng et al. 1996). It has also been suggested that host surface proteins bind to TM proteins of HIV-1 and HIV-2 (Chen et al. 1992; Ebenbichler et al. 1993; Ebenbichler et al. 1996).

Enveloped animal viruses may use similar strategies to enter cells. Their envelope proteins are remarkably similar in structure. For instance, crystal structure of hemaegglutinin of influenza virus is very similar to that of retrovirus envelope (Fass et al. 1996; Fass and Kim 1995). The TM proteins of retroviruses share many structural similarities. For instance, at linear sequence level, there is a stretch of hydrophobic amino acids at the N-terminus that is believed to be involved in the fusion of viral and cellular membranes. Another feature is the leucine zipper motif in the middle of TM proteins (Delwart and Mosialos 1990; Gallaher et al. 1989). They also share structural similarities (Blacklow et al. 1995; Fass et al. 1996; Fass and Kim 1995; Lu et al. 1995).

The functions of TM in viral replication have been studied. It has been shown that TM of Mo-MLV envelope forms oligomers using the yeast two-hybrid system. Deletion and mutational analysis indicate that the putative leucine zipper motif in the extracellular domain of TM is necessary and sufficient for the binding and that the first three repeats of the leucine zipper-like motif are the most important in mediating the interaction (Li et al. 1996).

The present invention provides two cellular proteins have been identified by their ability to interact with transmembrane (TM) protein of Moloney murine leukemia virus (Mo-MLV). They are termed envelope-interacting proteins (EIPs) (Table 1). The studies presented infra show that EIP-1 and EIP-3 can interact with TM protein in the yeast two-hybrid system. In an in vitro binding assay, EIP-1 and EIP-3 can directly bind to ecotropic retrovirus.

To test if the binding of EIPs to virus affects viral infectivity, viruses were incubated with EIPs prior to infection. It was found that EIP-1 and EIP-3 can significantly increase viral transduction efficiency of ecotropic retrovirus using NIH3T3 cell as a target. EIP-1 was also examined to determine if it could increase the infectivity of amphotropic virus, because TM proteins of both ecotropic and amphotropic viruses are basically the same. It was found that EIP-1 significantly enhances infectivity of amphotropic virus using NIH3T3 cells. Similar results were obtained using Hela cells, a human cell line, as target cells.

The present invention provides genes designated EIP-1 and EIP-3 which encode envelope-interacting proteins, EIP-1 and EIP-3, respectively. EIP-1 and EIP-3 proteins interact with the TM envelope to enhance retrovirus infectivity (titer) when these proteins are added to a virus preparation, thereby providing an alternative to increase efficiency of retroviral gene delivery. The proteins provided by the present invention overcome the above-described problems associated with polybrene by increasing stimulation of gene transfer. Accordingly, EIP-1 and EIP-3 of the present invention also provides methods to enhance viral transduction in gene therapy.

SUMMARY OF THE INVENTION

This invention provides an isolated nucleic acid molecule encoding a envelope-interacting protein-1. This invention provides an isolated nucleic acid molecule which encodes an EIP-1 comprising an amino acid sequence as set forth in FIGS. 2A–2D.

This invention provides a fusion protein comprising an EIP-1 or a fragment thereof and a second peptide.

This invention provides a vector comprising the isolated nucleic acid molecule, wherein the encoded mammalian EIP-1 comprises the nucleic acid sequence set forth in FIGS. 2A–2D. This invention provides a plasmid designated pCGN-EIP-1 (ATCC Designation No. 209885).

This invention provides a method of producing an EIP-1, which comprises growing a host cell comprising vectors of the invention under suitable conditions permitting production of the EIP-1.

This invention provides an isolated nucleic acid molecule encoding a envelope-interacting protein-3. This invention provides an isolated nucleic acid molecule which encodes an EIP-3 comprising an amino acid sequence as set forth in FIGS. 3A–3E.

This invention provides a fusion protein comprising an EIP-3 or a fragment thereof and a second peptide.

This invention provides a vector comprising the isolated nucleic acid molecule, wherein the encoded mammalian EIP-3 comprises the nucleic acid sequence set forth in FIGS. 3A–3E. This invention provides a plasmid designated pCGN-EIP-3 (ATCC Designation No. 209884).

This invention provides a purified mammalian EIP-1.

This invention provides a protein designated EIP-1 comprising substantially the amino acid sequence set forth in FIGS. 2A–2D.

This invention provides a protein designated EIP-1 having the amino acid sequence set forth in FIGS. 2A–2D.

This invention provides a purified mammalian EIP-3.

This invention provides a protein designated EIP-3 comprising substantially the amino acid sequence set forth in FIGS. 3A–3E.

This invention provides a protein designated EIP-3 having the amino acid sequence set forth in FIGS. 3A–3E.

This invention provides an oligonucleotide comprising a nucleic acid molecule of at least 15 nucleotides capable of specifically hybridizing with a unique sequence included within the sequence of the isolated nucleic acid molecule encoding mammalian EIP-1, wherein the nucleic acid molecule comprises the nucleic acid sequence set forth in FIGS. 2A–2D.

This invention provides an oligonucleotide comprising a nucleic acid molecule of at least 15 nucleotides capable of specifically hybridizing with a unique sequence included within the sequence of the isolated nucleic acid molecule encoding mammalian EIP-3 wherein the nucleic acid molecule comprises the nucleic acid sequence set forth in FIGS. 3A–3E.

This invention provides a monoclonal antibody directed to an epitope of an EIP-1.

This invention provides an antibody capable of binding to the EIP-3 having the amino acid sequence set forth in FIGS. 3A–3E or to a fusion protein thereof.

This invention provides a monoclonal antibody directed to an epitope of an EIP-3.

This invention provides a method of increasing transduction efficiency of a retrovirus on target cells comprising: a) incubating an envelope-interacting protein with a retrovirus; and b) transducing the target cells with the retrovirus.

This invention provides a method of increasing transduction efficiency of a retrovirus on a target cell comprising: a) incubating an envelope-interacting protein with a target cell; and b) transducing the target cell with a retrovirus.

This invention provides a method of treating a patient with a therapeutic gene comprising: a) incubating a transducing virus with an effective amount of an envelope-interacting protein effective to enhance retroviral infectivity; and b) transducing target cells of the patient with the resulting virus of step (a) bound to the envelope-interacting protein comprising a therapeutic gene, thereby treating the patient with the therapeutic gene.

This invention provides a method of treating a patient with a therapeutic gene comprising: a) incubating a transducing virus with an effective amount of an envelope-interacting protein effective to enhance retroviral infectivity; and b) transducing target cells of the patient with a retroviral virion plus the envelope-interacting protein bound thereto, comprising a therapeutic gene, thereby treating the patient with the therapeutic gene.

This invention provides a method of treating a patient with a therapeutic gene comprising: a) incubating a retroviral virion comprising a therapeutic gene with an effective amount of an envelope-interacting protein to permit enhanced binding of the envelope-interacting protein to the virion; and b) transducing target cells of the patient with the envelope-interacting protein bound virion comprising the therapeutic gene, thereby treating the patient with the therapeutic gene.

This invention provides a pharmaceutical composition comprising an envelope-interacting protein bound retroviral virion comprising a therapeutic gene and a pharmaceutically acceptable carrier capable of passing through a cell membrane. This invention provides a pharmaceutical composition comprising an amount of an envelope-interacting protein bound retroviral virion comprising a therapeutic gene effective to enhance retroviral infectivity of target cells and a pharmaceutically acceptable carrier capable of passing through a cell membrane.

This invention provides a method of treating an abnormality in a subject, wherein the abnormality is alleviated by the administering to the subject an effective amount of any of the above-described pharmaceutical compositions effective to introduce high titers of a therapeutic gene to the subject, thereby treating the abnormality in the subject.

BRIEF DESCRIPTION OF THE FIGURES

FIGS. 2A–2D EIP-1 full-length DNA sequence of 1536 base pairs is shown. Three-phase translation is shown below the DNA sequence (three reading frames) (SEQ ID NOS: 2–). The encoded protein EIP-1 is shown directly below the DNA sequence; the first amino acid of the coding region, Met, is boxed and as is the stop codon.

FIGS. 3A–3E EIP-3 full-length DNA sequence of 1735 base pairs is shown. Three-phase translation is shown below the DNA sequence (three reading frames). The encoded protein EIP-3 is shown in the third row of amino acids below the DNA sequence (SEQ ID NO :5); the first amino acid of the coding region, Met, is boxed and as is the stop codon.

FIG. 5 Summary of Envelope-Interacting Proteins (EIPs). The LexABD-TM3 fusion protein, the bait used in the yeast two-hybrid screening, contains the extracellular portion of the envelope TM protein (TM3) fused to the C-terminus of the DNA-binding domain of transcription factor LexA. To screen the cDNA library, yeast strain CTY10-5d was sequentially transformed with LexABD-TM3 and DNA from pools of plasmids containing WEHI-3 cDNA, and co-transformants were selected for histidine and leucine prototrophy. Interactions of TM3 with proteins expressed from the cDNA library led to transcriptional activation of the LacZ gene integrated into the yeast host strain genome beta-galactosidase assay was performed to identify clones that turned blue in the presence of X-Gal. Plasmids containing these cDNAs of host proteins were then isolated from blue colonies. Partial sequences of these clones were obtained and used to search Genbank.

FIG. 6 Specificity of interactions between EIPs and TM3. EIP-Gal4 transcription activation domain fusion proteins were cotransformed with Gal4 DNA binding domain fused with TM3, laminin, Gal4 DNA binding domain alone, and null (no DNA) into yeast strain SFY526. LacZ expression was determined by X-Gal assay. TM3, the extracellular domain of TM. +, stained blue; –, white with X-Gal stain.

FIG. 7A. The specification, inter alia, at Example 3 provides a detailed description of the binding assay. FIG. 7B. Bar graph illustrates that virus binding to EIPs (GST-EIP-1) leads to a reduction in virus titer in supernatant as compare to the virus titer with GST beads alone. Significantly fewer colonies are formed using GST-EIP-1.

DETAILED DESCRIPTION OF THE INVENTION

Figure 1:
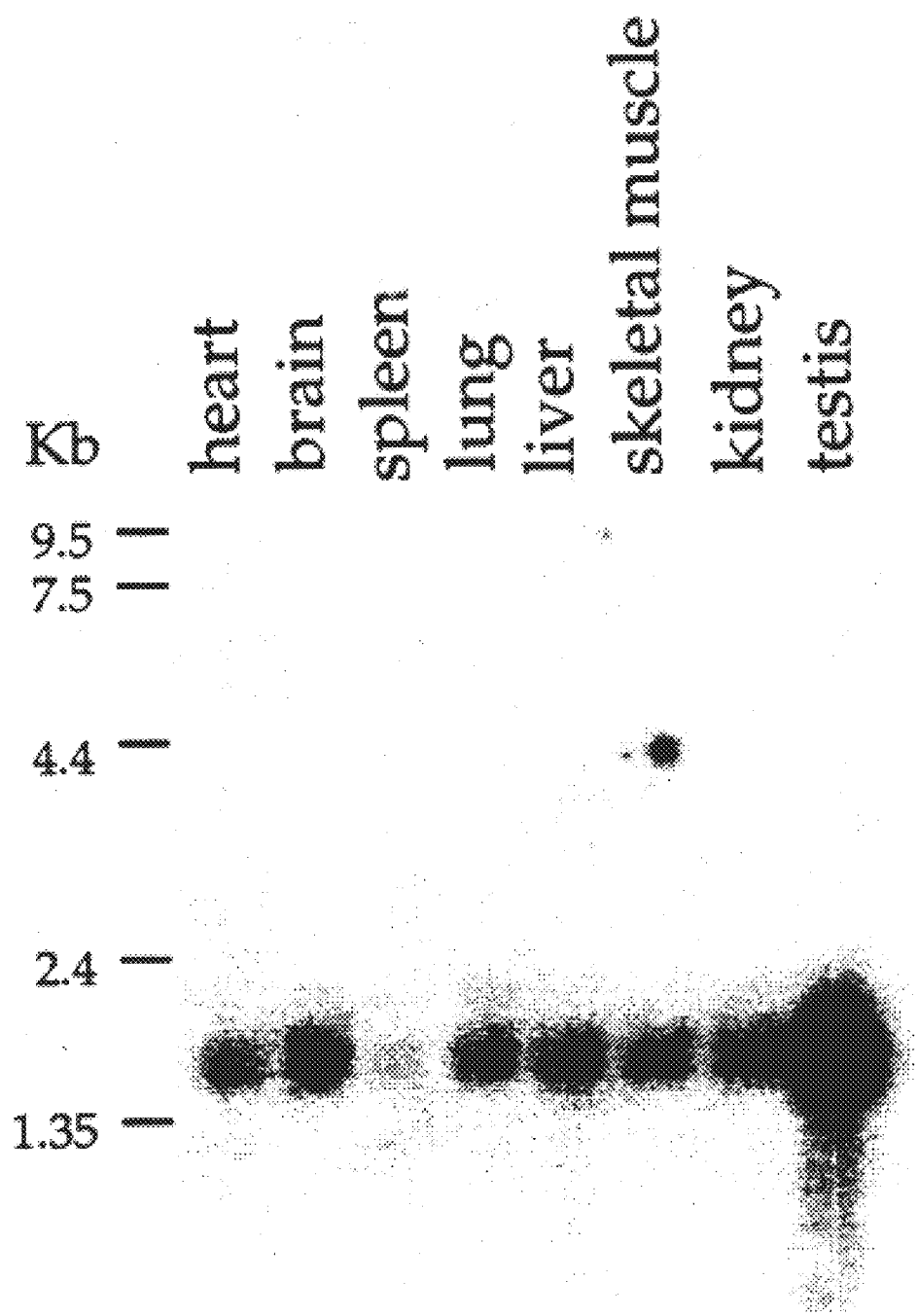
FIG. 1 EIP-1 mRNA Expression Pattern. The expression of EIP-1 mRNA in various mouse tissues: heart, brain, spleen, lung, liver, skeletal muscle, kidney and testis is shown.

The following standard abbreviations are used throughout the specification to indicate specific nucleotides:

C=cytosine A=adenosine

T=thymidine G=guanosine

This invention provides an isolated nucleic acid molecule encoding a envelope-interacting protein-1. The envelope-interacting protein-1 designated EIP-1, encoded by the isolated nucleic acid molecule binds to the transmembrane protein of Moloney murine leukemia virus. In an embodiment the host protein EIP-1 is a mammalian protein. In a another embodiment the host protein EIP-1 is a mouse protein. In another embodiment the host protein EIP-1 is a human protein. In a further embodiment the isolated nucleic acid molecule of claim 1, wherein the nucleic acid molecule is a DNA molecule. In an embodiment the above-described isolated DNA molecule is a cDNA molecule. In a still further embodiment the above-described isolated DNA molecule is a genomic DNA molecule. In a another embodiment the the above-described isolated nucleic acid is an RNA molecule.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptides, envelope-interacting protein-1 and envelope-interacting protein-3 (EIP-3), infra., and as products for the large scale synthesis of the polypeptides (EIP-3 and EIP-3) by a variety of recombinant techniques. The molecule is useful for generating new cloning and expression vectors, transformed and Ad transfected prokaryotic and eukaryotic host cells, and new and useful methods for cultured growth of such host cells capable of expression of the polypeptides (EIP-3 and EIP-3) and related products.

In a further embodiment the isolated nucleic acid molecule encodes a mammalian EIP-1. In an embodiment of the above-described isolated nucleic acid molecule, the encoded mammalian EIP-1 is a human, mouse or rat envelope-interacting protein. In a further embodiment the isolated nucleic acid molecule encodes an EIP-1 comprising an amino acid sequence as set forth in FIGS. 2A–2D. In another embodiment the above-described isolated nucleic acid molecule encodes an EIP-1, wherein the EIP-1 has substantially the same amino acid sequence as set forth in FIGS. 2A–2D. In an embodiment the above-described isolated nucleic acid molecule encodes an EIP-1, wherein the EIP-1 has the amino acid sequence as set forth in FIGS. 2A–2D. In an embodiment of the above-described isolated nucleic acid molecule the encoded mammalian EIP-1 comprises the nucleic acid sequence set forth in FIGS. 2A–2D. In a further embodiment any of the above-described isolated nucleic acid molecule may be operatively linked to a promoter of RNA transcription.

This invention provides a fusion protein comprising an EIP-1 or a fragment thereof and a second peptide. In an embodiment of the fusion protein, the second peptide is GST and the fusion protein is designated GST-EIP-1.

This invention provides a vector comprising the isolated nucleic acid molecule, wherein the encoded mammalian EIP-1 comprises the nucleic acid sequence set forth in FIGS. 2A–2D. In an embodiment of the vector, the vector is adapted for expression in a host cell which comprises the regulatory elements necessary for expression of the nucleic acid molecule in the host cell operatively linked to the nucleic acid molecule encoding the EIP-1 as to permit expression of the EIP-1. In a further embodiment of the vector, the host cell is a eukaryotic, bacterial, insect or yeast cell. In another embodiment of the vector the eukaryotic host cell is a mammalian cell. In an embodiment the vector is a plasmid. In a preferred embodiment the plasmid is designated pCGN-EIP-1 (ATCC Designation No. 209885). pCGN-EIP-1 comprises the full-length coding sequence of EIP-1.

In an embodiment, a full-length cDNA coding sequence of an EIP-1 nucleic acid molecule encoding a mouse EIP-1 is inserted into an *E.coli* plasmid and the resulting plasmid is designated as pCGN-EIP-1. Plasmid pCGN-EIP-1 was deposited on May 20, 1998, 1998, with the American Type Culture Collection (ATCC), 10808 University Boulevard, Manassas, Va. 20110-2209, U.S.A. under the provisions of the Budapest Treaty for the International Recognition of the Deposit of Microorganisms for the Purposes of Patent Procedure. Plasmid pCGN-EIP-1 was accorded ATCC Designation No. 209885.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

One of ordinary skill in the art will easily obtain unique sequences from the cDNA cloned in the pCGN-EIP-1 or pCGN-EIP-3 plasmids. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the pCGN-EIP-1 or pCGN-EIP-3 plasmid may further be used to screen other human tissue cDNA libraries to obtain isoforms of the nucleic acid sequences encoding EIP-1 and EIP-3, respectively, as well as to screen human genomic DNA to obtain the analogous nucleic acid sequences. The homologous nucleic acid sequences and isoforms may be used to produce the proteins encoded thereby.

This invention provides a plasmid comprising the nucleic acid molecule encoding a mouse EIP-1 designated pCGN-EIP-1 (ATCC Designation No. 209885).

This invention provides a nucleic acid probe comprising a nucleic acid molecule of at least 15 nucleotides capable of specifically hybridizing with a unique sequence included within the sequence of an isolated nucleic acid molecule encoding a mouse EIP-1. The nucleic acid probe may hybridize to any of the above-described isolated full-length nucleic acid molecules encoding a mammalian EIP-1 or fragments thereof. As used herein, mammalian EIP-1 includes but is not limited to murine and human EIP-1.

This invention provides a nucleic acid probe comprising a nucleic acid molecule of at least 15 nucleotides which is complementary to a sequence of the isolated nucleic acid molecule encoding a mammalian EIP-1.

The nucleic acid probe is complementary to a sequence of any of the above-described isolated full-length nucleic acid molecules encoding a mammalian EIP-1 or fragments thereof.

This invention provides a method of producing an EIP-1, which comprises growing a host cell comprising any of the above-described vectors under suitable conditions permitting production of the EIP-1. In an embodiment the method further comprises recovering the EIP-1 so produced. In a further embodiment of the above-described method, the method further comprises purifying the recovered EIP-1.

This invention provides a method of producing a polypeptide having the biological activity of a protein encoded by the nucleic acid molecule encoding a EIP-1 which comprises growing host cells comprising any of the above-describer vectors under suitable conditions permitting production of the polypeptide and recovering the polypeptide so produced. In an embodiment the method further comprises purifying the recovered polypeptide.

This invention provides an isolated nucleic acid molecule encoding a envelope-interacting protein-3. The envelope-interacting protein-3 designated EIP-3, encoded by the isolated nucleic acid molecule binds to the transmembrane protein of Moloney murine leukemia virus. In an embodiment the host protein EIP-3 is a mammalian protein. In a further embodiment the host protein EIP-3 is a mouse protein. In another embodiment the host protein EIP-3 is a human protein. In an embodiment of any of the above-described isolated nucleic acid molecule, the nucleic acid molecule is a DNA molecule. In a further embodiment the DNA molecule is a cDNA molecule. In another embodiment of the isolated DNA molecule, the DNA molecule is a genomic DNA molecule. In an embodiment the isolated nucleic acid encoding a envelope-interacting protein-3 is an RNA molecule. In another embodiment the above-described isolated nucleic acid molecule encodes a mammalian EIP-3. In a further embodiment of the isolated nucleic acid molecule, the mammalian EIP-3 is a human, mouse or rat envelope-interacting protein. In an embodiment of the above-described isolated nucleic acid molecule, the nucleic acid molecule encodes an EIP-3 comprising an amino acid sequence as set forth in FIGS. 3A–3E. In an embodiment of the above-described the nucleic acid molecule, the nucleic acid molecule encodes an EIP-3, wherein the EIP-3 has substantially the same amino acid sequence as set forth in FIGS. 3A–3E. In another embodiment of the isolated nucleic acid molecule, the nucleic acid molecule encodes an EIP-3, wherein the EIP-3 has the amino acid sequence as set forth in FIGS. 3A–3E. In an embodiment of the above-described isolated nucleic acid molecule, the mammalian EIP-3 comprises the nucleic acid sequence set forth in FIGS. 3A–3E. In an embodiment of any of the above-described isolated nucleic acid molecules, the nucleic acid molecule may be operatively linked to a promoter of RNA transcription.

This invention provides a fusion protein comprising an EIP-3 or a fragment thereof and a second peptide. In an embodiment of the fusion protein, the second peptide is GST and the fusion protein is designated GST-EIP-3.

This invention provides a vector comprising the isolated nucleic acid molecule, whererin the encoded mammalian EIP-3 comprises the nucleic acid sequence set forth in FIGS. 3A–3E. In an embodiment the vector is adapted for expression in a host cell which comprises the regulatory elements necessary for expression of the nucleic acid molecule in the host cell operatively linked to the nucleic acid molecule encoding the EIP-3 as to permit expression of the EIP-3. In another embodiment of the vector, the host cell is a eukaryotic, bacterial, insect or yeast cell. In a further embodiment of the vector the eukaryotic host cell is a mammalian cell. In an preferred embodiment the vector is a plasmid. In a preferred embodiment the plasmid designated pCGN-EIP-3 (ATCC Designation No. 209884).

In an embodiment, a full-length cDNA coding sequence of an EIP-3 nucleic acid molecule encoding a mouse EIP-3 is inserted into an *E. coli* plasmid and the resulting plasmid is designated as pCGN-EIP-3. Plasmid pCGN-EIP-3 was deposited on May 20, 1998, 1998 with the American Type Culture Collection (ATCC), 10808 University Boulevard, Manassas, Va. 20110-2209, U.S.A. under the provisions of the Budapest Treaty for the International Recognition of the Deposit of Microorganisms for the Purposes of Patent Procedure. Plasmid pCGN-EIP-3 was accorded ATCC Designation No. 209884.

This invention provides a plasmid comprising the nucleic acid molecule encoding a mouse EIP-3 designated pCGN-EIP-3 (ATCC Designation No. 209884).

This invention provides a nucleic acid probe comprising a nucleic acid molecule of at least 15 nucleotides capable of specifically hybridizing with a unique sequence included within the sequence of an isolated nucleic acid molecule encoding a mouse EIP-3. The nucleic acid probe may hybridize to any of the above-described isolated full-length nucleic acid molecules encoding a mammalian EIP-3 or fragments thereof. As used herein, mammalian EIP-3 includes but is not limited to murine and human EIP-3.

This invention provides a nucleic acid probe comprising a nucleic acid molecule of at least 15 nucleotides which is complementary to a sequence of the isolated nucleic acid molecule encoding a mammalian EIP-3.

The nucleic acid probe is complementary to a sequence of any of the above-described isolated full-length nucleic acid molecules encoding a mammalian EIP-3 or fragments thereof.

This invention provides a method of producing an EIP-3, which comprises growing a host cell comprising any of the above-described vectors under suitable conditions permitting production of the EIP-3. In an embodiment the method further comprises recovering the EIP-3 so produced. In a further embodiment the method, further comprises purifying the recovered EIP-3.

This invention provides a method of producing a polypeptide having the biological activity of a protein encoded by the nucleic acid molecule encoding a EIP-3 which comprises growing host cells comprising any of the above-described vectors under suitable conditions permitting production of the polypeptide and recovering the polypeptide so produced. In an embodiment the method further comprises purifying the recovered polypeptide.

This invention provides a purified mammalian EIP-1. In an embodiment the purified mammalian EIP-1 which is a human EIP-1. In another embodiment the purified mammalian EIP-1 is a murine EIP-1.

This invention provides a protein designated EIP-1 comprising substantially the amino acid sequence set forth in FIGS. 2A–2D.

This invention provides a protein designated EIP-1 having the amino acid sequence set forth in FIGS. 2A–2D.

This invention provides a purified mammalian EIP-3. In an embodiment the purified mammalian EIP-3 is a human EIP-3. In another embodiment the purified mammalian EIP-3 is a murine EIP-3.

This invention provides a protein designated EIP-3 comprising substantially the amino acid sequence set forth in FIGS. 3A–3E.

This invention provides a protein designated EIP-3 having the amino acid sequence set forth in FIGS. 3A–3E.

This invention provides an oligonucleotide comprising a nucleic acid molecule of at least 15 nucleotides capable of specifically hybridizing with a unique sequence included within the sequence of the isolated nucleic acid molecule encoding mammalian EIP-1, wherein the nucleic acid molecule comprises the nucleic acid sequence set forth in FIGS. 2A–2D. In an embodiment of the above-described oligonucleotide the nucleic acid is DNA. In another embodiment of the oligonucleotide the nucleic acid is RNA.

This invention provides an oligonucleotide comprising a nucleic acid molecule of at least 15 nucleotides capable of specifically hybridizing with a unique sequence included within the sequence of the isolated nucleic acid molecule encoding mammalian EIP-3 wherein the nucleic acid molecule comprises the nucleic acid sequence set forth in FIGS. 3A–3E. In an embodiment of the above-described oligonucleotide the nucleic acid is DNA. In another embodiment of the oligonucleotide is the nucleic acid is RNA.

This invention provides an antisense oligonucleotide comprising a sequence capable of specifically hybridizing with a unique sequence included within the above-described RNA molecule encoding an envelope-interacting protein-1.

This invention provides an antisense oligonucleotide comprising a sequence capable of specifically hybridizing with a unique sequence included within the above-described genomic DNA molecule encoding an envelope-interacting protein-1.

This invention provides an antisense oligonucleotide comprising a sequence capable of specifically hybridizing with a unique sequence included within the above-described RNA molecule encoding an envelope-interacting protein-3.

This invention provides an antisense oligonucleotide comprising a sequence capable of specifically hybridizing with a unique sequence included within the above-described genomic DNA molecule encoding an envelope-interacting protein-3.

This invention provides an antibody capable of binding to any of the above-described EIP-1 or to a fusion protein thereof. In an embodiment of the above-described antibody, the fusion protein is GST-EIP-1. In another embodiment of the above-described antibody, the antibody is a monoclonal antibody. In a further embodiment of the above-described antibody, the antibody is a polyclonal antibody.

This invention provides a monoclonal antibody directed to an epitope of an EIP-1.

This invention provides an antibody capable of binding to the EIP-3 having the amino acid sequence set forth in FIGS. 3A–3E or to a fusion protein thereof. In an embodiment of the above-described antibody, the fusion protein is GST-EIP-3. In another embodiment of the antibody, the antibody is a monoclonal antibody. In a further embodiment of the antibody, the antibody is a polyclonal antibody. This invention provides a monoclonal antibody directed to an epitope of an EIP-3.

Polyclonal antibodies may be produced by injecting a host animal such as rabbit, rat, goat, mouse or other animal with the immunogen of this invention, e.g. a purified mammalian EIP-1 or EIP-3 or a purified human EIP-1 or EIP-3. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice or rabbit with an immunogen. The mice or rabbits are inoculated intraperitoneally with an immunogenic amount of the above-described immunogen and then boosted with similar amounts of the immunogen. Spleens are collected from the immunized mice or rabbits a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC), 10808 University Boulevard, Manassas, Va. 20110-2209, USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides a method of increasing transduction efficieny of a retrovirus on target cells comprising: a) incubating an envelope-interacting protein with a retrovirus; and b) transducing the target cells with the retrovirus. In an embodiment of the above-described method, the envelope-interacting protein is envelope-interacting protein-1 or a fusion protein thereof. In another embodiment of the above-described method, the envelope-interacting protein is envelope-interacting protein-3 or a fusion protien thereof. In a preferred embodiment of the method, the retrovirus is an amphotropic virus. In another preferred embodiment the target cells are human cells or murine cells. In another preferred embodiment the retrovirus is an ecotropic virus. In an embodiment of the method wherein the retrovirus is an ecotropic virus, the target cells are murine cells. In another embodiment of the method, the retrovirus is an a Moloney murine leukemia virus (Mo-MLV). In a further embodiment of the method, the incubation is in vitro. In a still further embodiment of the method, the incubation is in vivo.

This invention provides a method of increasing transduction efficieny of a retrovirus on a target cell comprising: a) incubating an envelope-interacting protein with a target cell; and b) transducing the target cell with a retrovirus. In an embodiment of the method, wherein the envelope-interacting protein is envelope-interacting protein-1 or a fusion protein thereof. In another embodiment of the method, the envelope-interacting protein is envelope-interacting protein-3 or a fusion protein thereof. In a further embodiment of the method, the retrovirus is an amphotropic virus. In a preferred embodiment of the method, the retrovirus is an ecotropic virus. In a further preferred embodiment the incubation is in vitro. In a still preferred embodiment the incubation is in vivo. In a most preferred embodiment of the above-described methods the target cells are human cells. In the most preferred embodiment of the methods the human cells are hematopietic cells. In an embodiment of the above-described methods other cells which may be used include but are not limited to hepatocytes and fibroblasts.

This invention provides a method of treating a patient with a therapeutic gene comprising: a) incubating a transducing virus with an effective amount of an envelope-interacting protein effective to enhance retroviral infectivity; and b) transducing target cells of the patient with the resulting virus of step (a) bound to the envelope-interacting protein comprising a therapeutic gene, thereby treating the patient with the therapeutic gene.

This invention provides a method of treating a patient with a therapeutic gene comprising: a) incubating a transducing virus with an effective amount of an envelope-interacting protein effective to enhance retroviral infectivity; and b) transducing target cells of the patient with a retroviral virion plus the envelope-interacting protein bound thereto, comprising a therapeutic gene, thereby treating the patient with the therapeutic gene.

In an embodiment of either of the above-described methods, the envelope-interacting protein is envelope-interacting protein-1, envelope-interacting protein-3, a fusion protein of envelope-interacting protein-1, or a fusion protein of envelope-interacting protein-3. In further embodiments of these methods, steps (a) and (b) are performed ex vivo. In still further embodiments of these methods, the methods further comprise reintroducing the transduced target cells of step (b) into the patient. In other embodiments of these methods, steps (a) and (b) are performed in vivo. The EIPs of the present invention may be preincubated with a transducing virus and the resulting mixture may be administered in vivo to target cells of a pateint. In further embodiments the transduction of the target cells of the patient is effected by administration of a vector comprising the retroviral virion comprising the therapeutic gene to the patient.

This invention provides a method of treating a patient with a therapeutic gene comprising: a) incubating a retroviral virion comprising a therapeutic gene with an effective amount of an envelope-interacting protein to permit enhanced binding of the envelope-interacting protein to the virion; and b) transducing target cells of the patient with the envelope-interacting protein bound virion comprising the therapeutic gene, thereby treating the patient with the therapeutic gene. In an embodiment of the above-described method, the envelope-interacting protein is envelope-interacting protein-1, envelope-interacting protein-3, a fusion protein of envelope-interacting protein-1, or a fusion protein of envelope-interacting protein-3. In another embodiment of the method, the target cells have been previously removed from the patient and step (b) is performed ex vivo, further comprising administering an effective amount of the transduced target cells to the patient. In a further embodiment of the method, step (b) is performed in vivo. In a still further embodiment of the method, the target cells of the patient are transduced by administration of a vector comprising a virion comprising a therapeutic gene to the patient.

This invention provides a pharmaceutical composition comprising an envelope-interacting protein bound retroviral virion comprising a therapeutic gene and a pharmaceutically acceptable carrier capable of passing through a cell membrane.

This invention provides a pharmaceutical composition comprising an amount of an envelope-interacting protein bound retroviral virion comprising a therapeutic gene effective to enhance retroviral infectivity of target cells and a pharmaceutically acceptable carrier capable of passing through a cell membrane.

This invention provides a method of treating an abnormality in a subject, wherein the abnormality is alleviated by the administering to the subject an effective amount of any of the above-described pharmaceutical compositions effective to introduce high titers of a therapeutic gene to the subject, thereby treating the abnormality in the subject. In an embodiment of the above-described method, the abnormality is an abnormality associated with lack of a gene, a defective gene or an insufficient production of a gene product. In a preferred embodiment of the method, the abnormality is cancer. Other abnormalities for which the above-described method of treating may be used include, but are not limited to, thalassemia, sickle cell anemia, and cystic fibrosis.

This invention provides a method of administering the above-described pharmaceutical compositions comprising an amount of any of the above-described EIPs, EIP-1- or EIP-3-bound transducing viruses, oligonucleotides or antibodies which are determined to be potentially therapeutic, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

The present invention also provides a pharmaceutical composition comprising a effective amount of any of the above-described EIPs, EIP-1- or EIP-3-bound transducing viruses, oligonucleotides or antibodies which are determined to be potentially therapeutic and a pharmaceutically acceptable carrier. In the subject invention an "effective amount" is any amount of the above-described EIPs, EIP-1- or EIP-3-bound transducing viruses, oligonucleotides or antibodies which are determined to be potentially therapeutic, which, when administered to a subject suffering from a disease or abnormality against which the above-described EIPs, EIP-1- or EIP-3-bound transducing viruses, oligonucleotides or antibodies which are determined to be potentially therapeutic, are effective, causes reduction, remission, or regression of the disease or abnormality.

In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above-described EIPs, EIP-1- or EIP-3-bound transducing viruses, oligonucleotides or antibodies which are determined to be potentially therapeutic can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above-described ligands, oligonucleotides or antibodies which are determined to be potentially therapeutic can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular EIPs, EIP-1- or EIP-3-bound transducing viruses, oligonucleotides or antibodies in use, the strength of the preparation, the mode of administration, and the advancement of the disease condition or abnormality. Additional factors depending on the particular subject being treated will result in a need to adjust dosages, including subject age, weight, gender, diet, and time of administration.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

MATERIALS AND METHODS

EXAMPLE 1

Characterization of EIP-1 and EIP-3

Expression patterns of EIP-1 and EIP-3. The expression pattern of EIP-1 and EIP-3 in tissues and cell lines is determined by using Northern blot analysis. Total RNA or poly A+ mRNA is isolated from different tissues and cell lines and is used in Northern blot analysis to determine the expression pattern of EIP-1 and EIP-3 mRNA.(Clontech) RNA preparations from mouse tissues were used herein. FIG. 1 illustrates EIP-1 mRNA expression in various tissues. Cells that express or do not express EIPs are identified, the latter being particularly useful in studying the role of EIPs in fusion.

Full-length sequences EIP-1 and EIP-3. Complete sequences of cDNAs of both EIP-1 (SEQ ID NO:1) and EIP-3 (SEQ ID NO:5) were obtained. (See FIGS. 2A–2D and 3A–3E). Partial sequences obtained from the yeast two-hybrid clones of EIP-1 (SEQ ID NO:1) and EIP-3 (SEQ ID NO:5) were applied to obtain the full-length sequences of EIP-1 and EIP-3 cDNAs using the RACE system (Clontech). The partial 3' sequences obtained from the yeast two-hybrid cDNA clones of EIP-1 and EIP-3 are also used in the RACE system (Clontech) to obtain the 5' end sequences of cDNAs.

Plasmids have been constructed which producing EIP-1 and EIP-3 fused with glutathione S-transferase (GST-EIP-1 and GST-EIP-3).

Preparation of anti-EIP-1 and EIP-3 sera. A procedure has been established to perform a large scale isolation of GST fusion proteins (Frangioni and Neel 1993; Li et al. 1997) and is used to isolate EIPs to obtain anti-EIPs antisera. Large scale preparation of GST-EIP-1 and GST-EIP-3 is performed. Purified GST-EIP-1 and EIP-3 is used to immunize rabbits to generate antibodies against EIP-1 and EIP-3. (Cacolico)

EXAMPLE 2

Isolation of Host Proteins (EIPs) that Interact with the Transmembrane Proteins (TM) of the Moloney Murine Leukemia Virus (Mo-MLV) Envelope The functions of TM in viral replication have been studied. Using the yeast two-hybrid system it has been shown that TM of Mo-MLV envelope forms oligomers. Deletion and mutational analysis indicate that the putative leucine zipper motif in the extracellular domain of TM is necessary and sufficient for the binding and that the first three repeats of the leucine zipper-like motif are the most important in mediating the interaction (Li et al. 1996). It has been proposed that besides viral receptors, other host factors are also involved in virus entry into cells.

Figure 4:
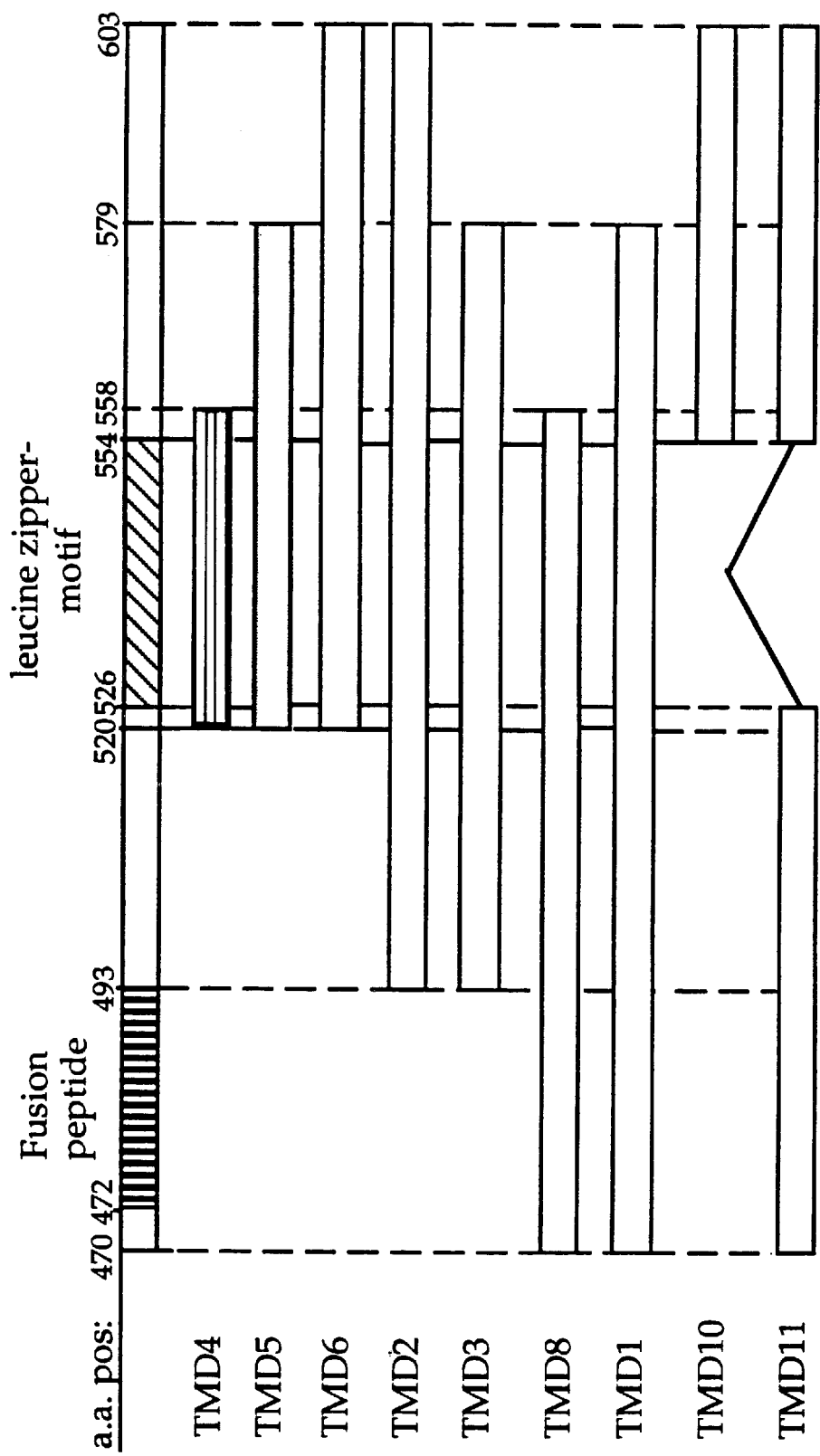
FIG. 4 Mapping EIP-1 sites to the transmembrane (TM) protein. A schematic diagram showing the extracellular domain of TM, with the fusion peptide and the leucine zipper-like motif indicated. Regions retained in the various deletion mutants are represented with bars, Black bar, no binding; gray bar, weak binding; and white bar strong binding.

FIG. 4 illustrates EIP-1 binding sites in the TM protein. The schematic diagram shows the extracellular domain of TM with the fusion peptide and the leucine zipper-like motif indicated. The regions retained in the various deletion mutants are represented with bars: black bar, no binding; gray bar, weak binding; white bar, strong binding.

The yeast two-hybrid system has been used both to study interactions between known proteins and to identify novel proteins that interact with "baits" (Li et al. 1996; Li et al. 1997). The yeast two-hybrid system was used to screen for host proteins that interact with TM protein of Mo-MLV. In total 11 host (mouse) envelope-interacting proteins (EIPs) that interact specifically with the TM protein of Mo-MLV have been identified and isolated using the yeast two-hybrid system (FIG. 5). Five EIP proteins (EIP-1 to EIP-5) were subsequently characterized. It was found that EIP-1 and EIP-3 significantly increase the transduction efficiency of retroviral vectors (see Table 2–6 infra).

The bait used in the yeast two-hybrid screening of the envelope-interacting proteins, LexABD-TM3, contains the extracellular portion of the envelope TM protein (TM3) fused to the C terminus of the DNA-binding domain of transcription factor LexA.

A cDNA library made from WEHI-3 cells was screened using the yeast strain CTY10-5d. Yeast strain CTY10-5d was sequentially transformed with LexABD-TM3 and DNA from pools of plasmids containing WEHI-3 cDNAs and cotransformants were selected for histidine and leucine prototrophy. Interactions of TM3 with proteins expressed from the cDNA library led to transcriptional activation of the LacZ gene integrated into the yeast host strain genome. A beta-galactosidase assay was performed to identify clones that turned blue in the presence of X-Gal. Plasmids containing these cDNAs of host proteins that interact with the TM were then isolated from positive (blue) colonies. Partial sequences of these clones were obtained and used to search Genbank.

Approximately 4 million independent cDNAs have been screened and 41 clones recovered falling into 11 groups (FIG. 5). All cDNA clones were subjected to and passed several tests in the yeast two-hybrid system (Luban and Goff 1995).

Specificity of interactions between EIPs and TM3 are summarized in FIG. 6. EIP-Gal4 transcription activation domain fusion proteins were cotransformed with Gal4 DNA binding domain fused with TM3, laminin, Gal4 DNA binding domain alone, and null (no DNA) into yeast strain SFY526. LacZ expression was determined by the X-Gal assay. The results indicate that the interactions between EIPs and TM are specific (FIG. 6). The EIPs interact with TM3, not with the empty vector or a nonspecific protein. They are also not self-activating.

The specificity of interaction between EIP-1 and TM protein was extensively examined (Table 1). Plasmids encoding various DNA binding domain fusion proteins were co-transfected into yeast with transcriptional activation domain fusion of EIP-1. Interactions were scored by expression of beta-galactosidase measured by X-Gal assay. The results confirmed that EIP-1 specifically binds to TM. Partial sequences of all these clones have been obtained, and they appear to encode novel proteins (FIG. 5).

Figures 8A, 8B:
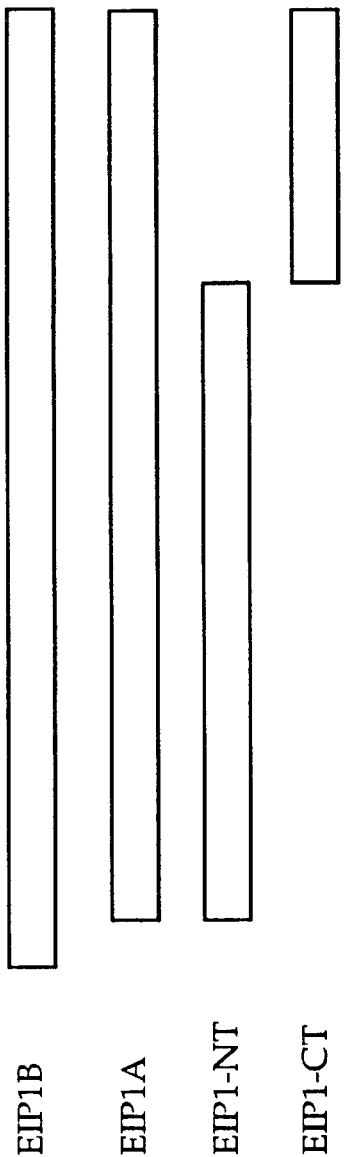
FIGS. 8A–8B Mapping the region in EIP-1 that mediates the interaction between EIP-1 and TM using the yeast two-hybrid system. Determination of the binding domain in EIP-1 with TM proteins of Mo-MLV, EIP-1, the original isolate from the yeast two-hybrid screening; EIP-1-NT, the N-terminal portion of EIP-1 (containing region from the N-terminus to the putative transmembrane domain of EIP-1); EIP-CT, the C-terminal portion of EIP-1, region after putative transmembrane domain of EIP-1 to the C-terminus. +++, stained blue one hour after staining; ++, stained blue four hours after staining; −, stained white 20 hours after staining.
Figure 9:
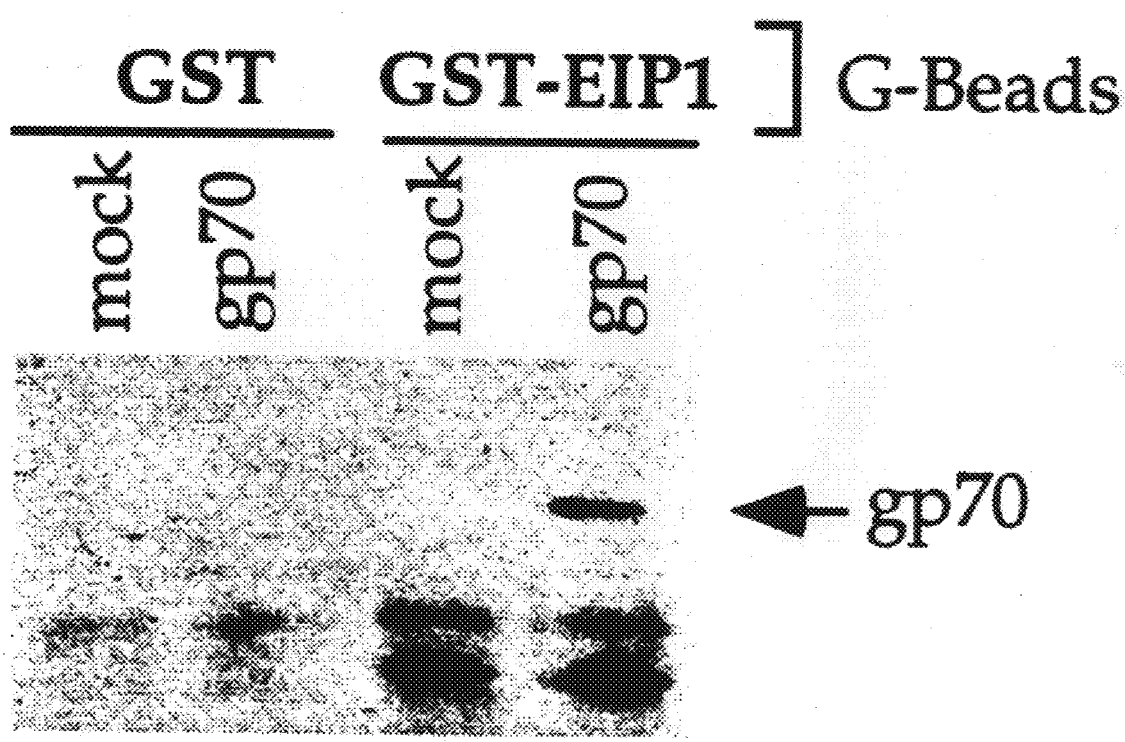
FIG. 9 Pull-down of Mo-MLV envelope protein with recombinant GST-EIP-1. Recombinant GST proteins were expressed in DH5α and bound to agarose-gluthione beads at 4° C. for one hour. The beads were then washed with PBS three times and ready for use. Envelope protein of MoMLV, gp70 was tagged with myc epitope and expressed in COS-7 cells. Cells were lysed in TNEN lysis buffer containing 100 mM NaCl, 50 mM Tris-HCl, 10 mM EDTA and 0.5% NP-40. 500 μg of the lysate protein were incubated with the GST protein bound agarose beads for one hour at 4° C., followed by a wash with TNEN three times. Proteins bound on the beads were boiled off and subjected to 7.5% PAGE analysis. Proteins were detected by Western blot analysis with 9E10, a monoclonal antibody against myc epitope. The migration position of gp70 is indicated. Mock, mock transfection; gp70, transfection with plasmid expressing myc tagged gp70.

FIGS. 8A–8B illustrate the mapping region in EIP-1 that mediates the interaction between EIP-1 and TM. FIG. 9 demonstrates binding of Mo-MLV envelope protein with recombinant GST-EIP-1. (See legends for respective method details)

TABLE 1

Specificity of interactions between TM and EIP-1

| Fusion proteins[a] | | Operator | β-Gal activity[b] |
|---|---|---|---|
| lexABD-TM3 | + GAL4AD-EIP-1 | lexA | ++ |
| lexABD-MG | + GAL4AD-EIP-1 | lexA | − |
| lexABD-Rb | + GAL4AD-EIP-1 | lexA | − |
| lexABD-130 | + GAL4AD-EIP-1 | lexA | − |
| lexABD | + GAL4AD-EIP-1 | lexA | − |
|  | GAL4AD-EIP-1 | lexA | − |
| GAL4BD-TM3 | + GAL4AD-EIP-1 | USA$_G$ | ++ |
| GAL4BD-p53 | + GAL4AD-EIP-1 | USA$_G$ | − |
| GAL4BD-cyto-KAE1 | + GAL4AD-EIP-1 | USA$_G$ | − |
| GAL4BD-KB3-C | + GAL4AD-EIP-1 | USA$_G$ | − |
| GAL4BD-D89 | + GAL4AD-EIP-1 | USA$_G$ | − |
| GAL4BD | + GAL4AD-EIP-1 | USA$_G$ | − |
|  | GAL4AD-EIP-1 | USA$_G$ | − |

[a]Plasmids encoding various DNA binding domain fusion proteins were co-transfected into yeast with transcriptional activation domain fusion of EIP-1. Interactions were scored by expression of beta-galactosidase measured by X-Gal assay. MG, gag protein of Moloney murine leukemia virus; Rb, retinoblastoma protein; p130, a member of RB family; cyto-KAE1, N-terminus of cytoplasmic domain of kAE1; KB3-C, N-terminus of cytoplasmic domain of kidney band 3; D89, a fragment of ankyrin.
[b]++, dark blue; +; blue, −white with X-Gal stain

EXAMPLE 3

EIP-1 and EIP-3 Bind to the Intact Virus

One major problem associated with the yeast two-hybrid system is the presence of false positives. Accordingly, the biological relevance of the envelope-interacting proteins (EIPs) has been determined by examining the ability of these EIPs to bind to the intact virus in an in vitro binding assay.

Figure 7A:
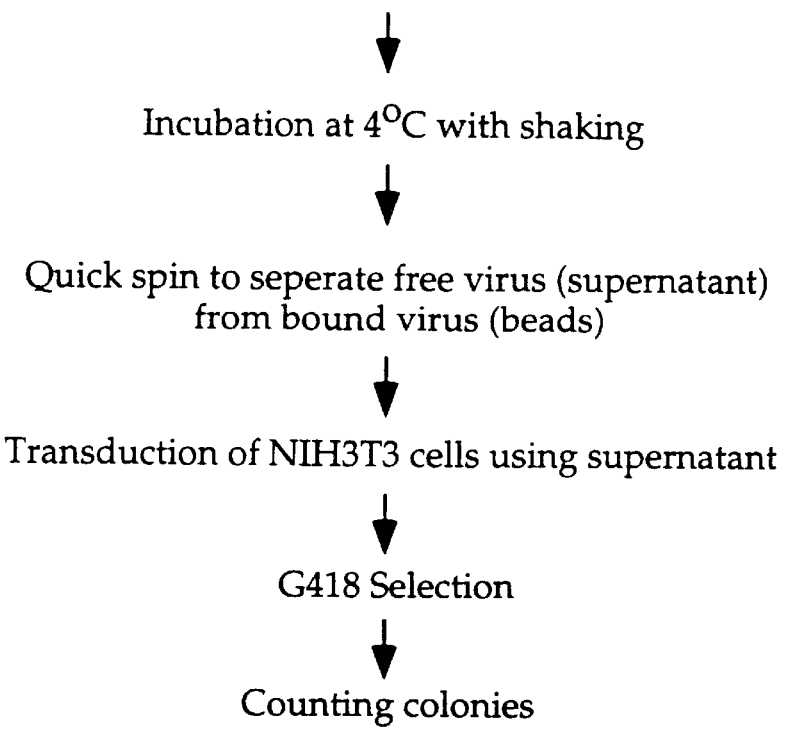
FIGS. 7A–7B Assay to determine EIPs binding to intact virus.

One assays that provides useful information is a detection of binding of the EIPs to the intact virus using a second, independent assay. In this assay (see FIG. 7A), a replication-defective virus, N2, was utilized (Markowitz et al. 1988b), which is prepared from a packaging cell line GP+E86+N2 and does not contain a complete viral genome. The replication-defective virus, N2, contains a neo resistance marker. Cells transduced by this virus can survive in medium containing G418. This virus provides two advantages over the wild type virus. First, since it cannot replicate, there is only one round of infection. This feature is particularly useful in studying early events of viral infection because there is no subsequent reinfection of cells by progeny virus. Second, cells transduced by N2 are neo resistant. Thus, the infection efficiency can be quantitated by counting the number of neo-resistant colonies.

Figure 7B:
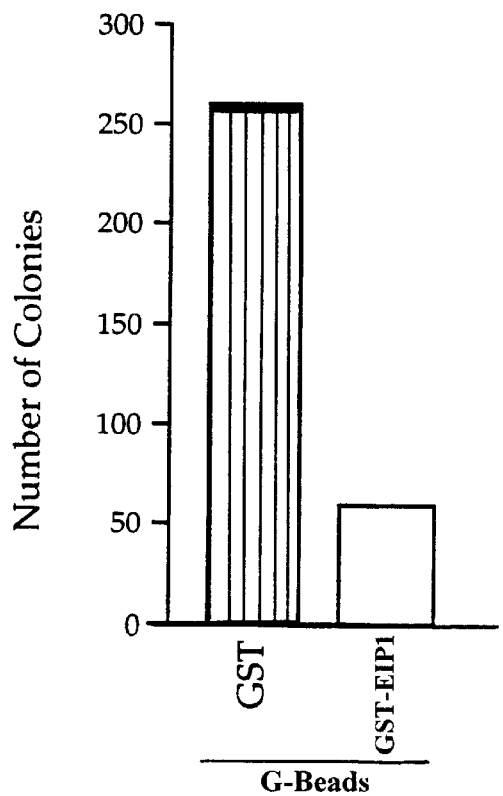

EIP-1 to EIP-5 have been examined using this assay to directly measure the binding of EIPs to the intact virus. In this binding assay, virus is mixed with GST-EIP-agarose beads and incubated for 2 hours. After incubation, the mixtures are centrifuged, and the supernatants are used to transduce fresh NIH3T3 cells. After two days, cells are split into G418-containing medium. Ten to twelve days later, colonies are counted. If the virus binds to EIPs, virus is retained on agarose beads leading to a reduction in virus titer in supernatant. The results indicate that agarose beads coupled with EIP-1, EIP-2 and EIP-3 decreased virus titer. In control samples, virus was incubated with GST-agarose beads or beads alone, and no change in virus titer was observed (Table 2). FIG. 7B shows agarose beads coupled with EIP-1 resulted in a fewer colonies than agarose beads with GST-agarose beads alone.

The results from this study indicated that EIP-1 and EIP-3 bound strongly to the intact virus (Table 2).

This assay directly examines the binding between EIPs and the TM in its natural state, i.e., in the context of the whole envelope protein. Thus, binding results obtained from this experiment provide physiologically relevant evidence.

TABLE 2

Effect of GST-EIP on viral infection of ecotropic virus[a]

| | Neo$^r$ Colonies | | |
|---|---|---|---|
| Treatment | 1:1 | 1:5 | Fold Increase |
| MEDIUM | 66 | 12 | 1 |
| GSH | 10 | 1 | 0.1 |
| GST | 58 | 8 | 1 |
| GST-EIP1$_B$ | >1000 | 353 | 30 |
| GST-EIP-2 | 69 | 24 | 1 |
| GST-EIP-3 | 360 | 95 | 5–8 |
| NO VIRUS | 0 | 0 | — |

[a]Effect of GST-EIP-1 on transuction of ecotropic virus on NIH3T3 cells. GST-EIPs was eluted with 5 mM glutathione in PBS from EIP-GST-agarose beads. GST-EIP was mixed with various amounts of N2 virus obtained from GP+E86+N2 cells cultures. Mixtures were incubated at 37° C. for 1 hour, and then added to NIH3T3 cells. After infection, residual virus was removed, and fresh medium was added. Cells were split 2 days later into G418-containinng medium and incuated from another 10 day period before scoring colonies. The results are from one typical experiment.

EXAMPLE 4

EIP-1 and EIP-3 Significantly Stimulate Viral Transduction Efficiencies

Since EIPs interact with the TM, it is possible that EIPs affect very early steps of viral infection. The second assay (see Example 3) is used to evaluate whether the interactions of EIPs with the TM fhave any effects on viral infection. GST-EIPs are eluted with 5 mM glutathione in phosphate-buffered saline (PBS) from GST-EIP-agarose beads. Purified GST-EIP is then mixed with various amounts of N2 virus (Markowitz et al. 1988b). Mixtures are incubated and then added to NIH3T3 cells. After infection, residual virus is removed, and fresh medium is added. Cells are split 2 days later into G418-containing medium and incubated for another 10–12 days before scoring colonies. Any effects of EIPs on infection are monitored by changes in the number of neo-resistant colonies.

Based on the results of the in vitro binding assay supra (Example 3), EIP-1, EIP-2 and EIP-3 were further tested using this assay. Purified EIP-1, EIP-2, and EIP-3, respectively, were incubated with an ecotropic virus, N2, that contains a neo marker instead of a complete viral genome. It was found that EIP-1 and EIP-3 increased infectivity of ecotropic N2 by a factor of 30 and 5–8, respectively (Table 2). EIP-2, however, showed no effects on virus infectivity in this assay.

EIP-1 was further studied to determine if it can increase infectivity of amphotropic virus. N2 virus prepared from packaging cell line AM12 (Markowitz et al. 1988a) was incubated with EIP-1 prior to transducing NIH3T3 cells. It was shown that EIP-1 also increased infectivity of amphotropic virus at least 5 fold using NIH3T3 as a target cell (Table 3). Similarly, it was shown that EIP-1 also increased infectivity of amphotropic virus at least 6-fold using both NIH3T3 cells and Hela cells as target cells (see for example Tables 4 and 5).

TABLE 3

Effect of GST-EIP-1 on viral infection of amphotropic virus[a]

| Treatment | Neo[r] Colonies 1:1 | 1:5 | Fold Increase |
|---|---|---|---|
| MEDIUM | 30 | 4 | |
| GSH | 76 | 33 | |
| GST | 112 | 16 | 1 |
| GST-EIP-1$_A$ | 854 | 136 | 7 |
| GST-EIP-1$_B$ | 403 | 102 | 5 |
| GST | 114 | 27 | 1 |
| NO VIRUS | 0 | 0 | — |

[a]GST-EIPS were eluted with 5 mM glutathione in PBS from EIP-GST-agarose beads. GST-EIP was mixed with various amounts of N2 virus obtained from AM12+N2 cell culture. Mixtures were incubated at 37° C. for 1 hour, and then added to NIH3T3 cells. After infection, residual virus was removed, and fresh medium was added. Cells were split 2 days later into G418-containingmedium and incubated from another 10 day period before scoring colonies. EIP-1A and EIP1B are two different clones of EIP-1, which were isolated independently. They have the same 3' end sequence, and EIP-1B has a longer 5' end sequence (about 50 bps).

TABLE 4

Effect of EIP1 on trasduction of amphotropic virus on NIH3T3 cells[a]

| | Neo[r] Colonies Amphotropic N2 virus | | |
|---|---|---|---|
| Treatment | 5 μl (1:10) | 5 μl (1:25) | Fold Increase |
| GST | 110 | 16 | 1 |
| GST-EIP1A | 854 | 136 | 8 |
| GST-EIP1B | 403 | 102 | 6 |

[a]Amphotropic N2 virus was prepared from the packaging cell line GP+envAm12+12, diluted and similarly treated with purified GST-EIP1 and GST as described in Materials and Methods.

TABLE 5

Effect of EIP-1 on transduction of amphotropic virus on Hela cells[a]

| | Neo[r] Colonies Amphotropic N2 virus | |
|---|---|---|
| Treatment | 5 μl (1:25) | Fold Increase |
| GST | 105 | 1 |
| GST-EIP-1B | 594 | 6 |

[a]Amphotric N2 virus was similarly prepared, diluted and treated with purified GST-EIP1 and GST proteins as described in Table 4. After incubation, whole mixtures were used to transduce Hela cells. Truced Hela cells were selected with G418, and resistant colonies were scored.

These results provide strong evidence that the binding between the TM and EIP-1 and EIP-3 are functionally relevant. This novel feature of EIP-1 and EIP-3 is to be further explored for potential application in gene therapy.

EXAMPLE 5

Determining Whether EIP-1 and EIP-3 Increase Transduction Efficiency of Retroviruses on Human Primary Cells EIP-1 and EIP-3 have been shown to increase transduction efficiency of both ecotropic and amphotropic retroviruses using NIH3T3 cells as target cells. EIP-1 has also been shown to be able to enhance virus titer of amphotropic virus using both NIH3T3 and Hela cell as target cells (supra). EIP-3 will be further determined if it enhances infectivity of amphotropic virus using both NIH3T3 and Hela cell as target cells. Furthermore, the study also demonstrates that EIP-1 and/or EIP-3 can enhance transduction efficiency of amphotropic viruses on primary human cells.

Assays as described supra will be employed to determine effects of EIP-1 and EIP-3 on transduction of primary human cells. Briefly, purified GST-EIP-1 and GST-EIP-3 are incubated with amphotropic viruses for one hour at 37° C. The mixtures are used to transduce human hematopoietic cells. Amphotropic viruses, N2, are prepared using AM12 (Markowitz et al. 1988a). As described supra, this virus does not contain a complete genome, instead, it contains a neo marker. The viral titer is directly scored by counting G418-resistant colonies after transduction and selection in G418-containing medium.

EXAMPLE 6

Determining the Effect of EIP-1 and EIP-3 on Retroviruses Pseudotyped with Other Viral Envelopes Besides amphotropic viruses, other viral envelope proteins such as VSV G and GALV envelope will be used to pseudotype murine retroviruses in gene therapy (Hopkins 1993; Porter et al. 1996; Sharma et al. 1996; Wang et al. 1996; Lam et al. 1996). Tests will be performed to determined if EIP-1 and/or EIP-3 can increase virus titers of vectors with such envelope proteins. It has been suggested that many unrelated enveloped animal viruses use similar strategies to enter cells (Blacklow et al. 1995; Delwart and Mosialos 1990; Fass et al. 1996; Fass and Kim 1995; Gallaher et al. 1989; Lu et al. 1995). This experiment will determine whether EIP-1 and EIP-3 exert similar stimulating effects on retroviruses pseudotyped with other viral envelope proteins.

Similar assays as described supra, will be done to determine effects of EIP-1 and EIP-3 on viruses with a different viral envelope proteins. An inducible VSV G protein expression system (GIBCO BRL) will be established and introduced into a packaging cell line. A virus containing VSV G protein and a neo marker will be prepared. This virus will be incubated separately with EIP-1 and EIP-3, and the effects of EIPs on transduction efficiency will be determined.

Retrovirus pseudotyped with envelope proteins of GALV envelope will be examined in a similar way. Although it is proposed that it is possible that EIP-1 and EIP-3 may work on those viruses, different conditions may be required for EIP-1 and EIP-3 to stimulate infectivity of viruses.

EXAMPLE 7

Determining Whether EIP-1 and EIP-3 have any Direct Effects on Cells

The mechanism of how EIP-1 and EIP-3 enhance viral infectivity is unknown. The stimulation of viral transduction by EIP-1 and EIP-3 could be a direct result of incubation of virus and either EIP-1 or EIP-3. Binding of EIP-1 or EIP-3 with retrovirus enables the retrovirus to infect cells more efficiently. It is also possible that stimulation of transduction efficiency by EIP-1 and/or EIP-3 is indirectly caused by modifications of target cells by EIPs. EIPs interact with target cells rendering them more susceptible to virus infection. Several approaches may be used to distinguish direct and indirect effects of EIPs.

First, EIP-1 and EIP-3 are added to cells with virus without prior incubation of EIPs with retroviruses. This determines whether incubation, i.e., the binding between EIPs with retroviruses before transduction will be necessary for the enhancing effects of EIPs. Furthermore, target cells are treated first with EIP-1 or EIP-3 prior to transduction by retroviruses. If the enhancing effects still can be observed, this will indicate that EIP-1 and EIP-3 exert an effect on cells, which increases susceptibility of target cells to viral transduction. To further determine if there is any cytotoxic effect of EIP-1 and/or EIP-3 on cells, a reporter gene will be introduced into target cells before cells are transduced by retroviruses with EIPs. Expression of the reporter gene will be is measured to determine cytotoxicity of EIPs on cells.

EXAMPLE 8

Determining Whether Anti-EIP Antibodies can Block Effects of EIP-1 and EIP-3

Anti-EIP-1 and anti-EIP-3 antisera are to be used to determine the specificity of the effects of EIP-1 and EIP-3. A series of dilutions of antisera will be prepared and used in incubation with EIPs and retroviruses. Prebleed sera will be similarly diluted and used as controls. Effects of EIPs on transduction efficiency in the presence of specific antisera are determined.

EXAMPLE 9

Determining Whether Partial EIP-1 and EIP-3 Proteins Without GST Portion have Higher Stimulating Efficiency Since GST is a rather large portion of GST-EIP-1 and GST-EIP-3 proteins, GST could affect interactions between EIP-1 and EIP-3, respectively, and retrovirus envelope proteins. The GST portion of GST-EIP-1 and GST-EIP-3 is cleaved off to determine whether EIP-1 and EIP-3 have a higher effect on viral transduction, i.e, increasing transduction efficiency.

The GST portion of GST-EIPs is cleaved using thrombin (Pharmacia), and EIPs are purified and used in a transduction enhancing assay according to previously described procedure, as described supra. EXAMPLE 10

Determining a Dosage Curve and Time Course of EIP-1 and EIP-3 Effects

This study will determine the optimal conditions for effects of EIP-1 and EIP-3 on transduction efficiency. GST-EIP-1 and EIP-3 will be prepared, and protein concentration will be determined by using a protein concentration standard and polyacrylamide gel that is stained with coomassie blue. Different amounts of EIP-1 and EIP-3 will be incubated with retrovirus at 37° C. for one hour, and the mixtures will be used to infect target cells. Two days after transduction, cells will be put into G418 selection, and G418-resistant colonies will be scored and used to determine enhancement of viral transduction by EIPs. Also EIP-1 and EIP-3 will be incubated with virus at 37° C. for different lengths of time, such as 0, 15, 30, 60 and 120 minutes, and the effects of EIP-1 and EIP-3, respectively, on transduction efficiency will be similarly determined.

In this study, different cell types and different viruses are to be tested. For particular cells, viruses or envelopes, different conditions are required. Thus the time course and dosage curve for each cell type and each virus is to be tested.

DISCUSSION

Two host proteins, EIP-1 and EIP-3 have been identified by their ability to interact with the transmembrane protein of Moloney murine leukemia virus (Mo-MLV). The initial characterization of EIP-1 and EIP-3, two of the env-interacting proteins indicated that they bind to the intact virus and significantly increase retroviral transduction efficiency of amphotropic and ecotropic retrovirus. Furthermore, it has been shown that EIP-1 can increase transduction efficiency of amphotropic retrovirus using both NIH3T3 cell and Hela cell, a human cell line as target cells. One of technical difficulties in application of gene therapy technology using retroviral vector is low titer of retroviral vector stocks. EIP-1 and EIP-3 can boost retroviral transduction efficiency of both ecotropic and amphotropic viruses, presenting a possible solution to such problem. Comprehensive analysis of EIP-1 and EIP-3 and the possibility of applying EIP-1 and EIP-3 in gene therapy are studied herein.

EIP-1: a TM-interacting Protein

It was found that the extracellular domain of TM could multimerize in yeast, and that this binding was affected by mutations in the critical 'leucine zipper' region (or '4-3 hydrophobic repeat') in accord with expectations based on the multimeric structure of the native protein (78). These results lead to screening of a library for TM-interacting proteins. A total of 48 clones, consisting of 12 novel genes, out of four million clones screened, were recovered. Studies were concentrated on one clone recovered 7 times, termed EIP-1 (for envelope interacting protein 1). The full-length cDNA of EIP-1 was recovered and sequenced. EIP-1 has no significant sequence similarity to any known gene, but has a potential membrane-spanning sequence near the C-terminus. The gene is expressed ubiquitously as a 1.8-kb mRNA.

EIP-1 interacts strongly with TM in the two-hybrid system, in either the LexA or Gal4DB system; it does not interact with control proteins, including Gag, p53, RB, p130, LexA, or Gal4DB. It was not self-activating in DNA-binding fusions. EIP-1 interaction with various fragments of TM was also tested, and two independently sufficient interaction domains that include the blocks on either side of the 'leucine zipper' region were identified; in contrast, the zipper region itself, which multimerizes with itself as well, showed no EIP-1 binding activity. Binding in vitro was confirmed: beads containing GST-EIP-1 bound the uncleaved gPr80$^{env}$ protein from lysates of COS cells, while those with GST alone did not.

Whether EIP-1 could interact with TM on the native virion particle was tested. GST-EIP-1 beads were incubated with preparations of a virus vector (N2) containing the neoR gene and pelleted, and the titer of the remaining virus was determined to test for depletion of infectivity from the stock. Whereas beads alone, beads containing GST, or beads with control GST fusions had no effect on the titer, beads with GST-EIP-1 could consistently reduce the titer approximately 4-fold.

In the case of HIV-1, a variety of proteins have been shown to affect virus infectivity and titer. Incubation of many strains with soluble CD4, the virus receptor, strongly inactivates virus; sometimes SU is stripped from the virus. Other strains are resistant, and, curiously, the infectivity of other viruses such as HIV-2 and SIV can be significantly enhanced by sCD4 (17). Some monoclonal anti-SU or anti-TM antibodies are virus-inactivating; but others can strongly enhance or potentiate virus infectivity (61, 74, 96, 102). To test for any such effects of EIP-1, GST-EIP-1 on glutathione beads was prepared, the protein EIP-1 was eluted, and the soluble protein was incubated with genetically marked virus preparations (N2 from GPE-86 cells). After incubation, the mixture was used to infect NIH/3T3 cells and the titer was determined. Incubation of GST-EIP-1 with virus reproducibly resulted in a dramatic increase in virus titer above controls; typically the titer rose 30-fold (Table 6). Control proteins, including GST and other GST-EIPs, had no effect.

TABLE 6

Enhancement of virus infectivity by GST-EIP-1. $Neo^r$ colonies resulting per plate after incubation of virus with purified protein (1 μg/ml) at 37° C. for 1 h.

| Treatment | CFU/10 ul virus | CFU/2 ul virus | Ratio |
|---|---|---|---|
| DMEM | 66 | 12 | 1 |
| DMEM+gluthathione | 10 | 1 | 0.1 |
| DMEM+GST | 58 | 8 | 1 |
| DMEM+GST-EIP-1 | >1000 | 353 | 30 |
| DMEM+GST-EIP-2 | 69 | 24 | 1 |
| no virus | 0 | 0 | — |

The increased infectivity of ecotropic viruses did not alter the host range; the stimulated virus still was restricted to mouse cells, and did not infect human cells. Similar, though somewhat more modest effects (5–8×), were seen with amphotropic viruses titered on human cells. This result is consistent with the fact that although these viruses use a different SU and receptor, the TM domain is interchangeable. The stimulation in titer mediated by EIP-1 occurred at very low concentrations (<0.1 ug/ml), with maximal increase at less than 1 ug/ml of protein, and was fairly slow, requiring about an hour for maximal increase. Thus, the stimulation was distinct from the nonspecific effects of facilitators such as polybrene, DEAE dextran, or histones (107) in its potency at far lower concentrations. The stimulation by EIP-1 was also apparently independent of polybrene in that the effects of the two were additive; EIP-1 gave a similar stimulation over baseline controls in the absence or presence of polybrene. The addition of very high concentrations of protein—more than 50 ug/ml—resulted in inhibition of infectivity.

The experiments presented herein demonstrate that EIP-1 and EIP-3 provide a clue to virus entry mechanisms and are useful adjuvants for viral gene transfer.

The observations supra of significant enhancement of viral transduction by EIP-1 and EIP-3 suggest the possible application of EIP-1 and EIP-3 in gene therapy to boost viral titer. It may be possible to apply EIP-1 and EIP-3 in increasing viral titer in gene therapy. Whether EIP-1 and EIP-3 have similar effects on infection of human primary cells by retroviral vectors must be determined. The scope of effects of EIP-1 and EIP-3 on commonly used retroviral vectors, such as amphotropic virus and retroviruses pseudotyped with other envelopes including VSV G and GALV envelope will also be determined.

REFERENCES

Anderson, W. F. (1984). Prospects for human gene therapy. Science, 226, 401–409.

Blacklow, S. C., Lu, M., and Kim, P. S. (1995). A trimeric subdomain of the simian immunodeficiency virus envelope glycoprotein. Biochemistry, 34, 14955–62.

Chen, Y. H., Ebenbichler, C., Vornhagen, R., Schulz, T. F., Steindl, F., Bock, G., Katinger, H., and Dierich, M. P. (1992). HIV-1 gp41 contains two sites for interaction with several proteins on the helper T-lymphoid cell line, H9. AIDS, 6, 533–539.

Cone, R. D., and Mulligan, R. C. (1984). High efficiency gene transfer into mammalian cels:generation of helper-free retrovirus with broad mammalian host range. Proc. natl. Acad. Sci. USA, 81, 6349–6353.

Cone, R. D., Weber-Benarous, A., Baorto, D., and Mulligan, R. C. (1987). Regulated expression of a complete human b-globin gene encoded by a transmissible retrovirus vector. Mol. Cell. Biol., 7, 887–897.

Delwart, R. L., and Mosialos, G. (1990). Retroviral envelope glycoproteins contain a leucine zipper like repeat. AIDS Res. Hum. Retroviruses, 6, 703–706.

Deng, H., Liu, R., Ellmeier, W., Choe, S., Unutmaz, D., Burkhart, M., Di Marzio, P., Marmon, S., Sutton, R. E., Hill, C. M., Davis, C. B., Peiper, S. C., Schall, T. J., Littman, D. R., and Landau, N. R. (1996). Identification of a major co-receptor for primary isolates of HIV-1. Nature, 381, 662–666.

Dragic, T., Litwin, V., Allaway, G. P., Martin, S. R., Huang, Y., Nagashima, K. A., Cayanan, C., Maddon, P. J., Koup, R. A., Moore, J. P., and Paxton, W. A. (1996). HIV-1 entry into CD4+ cells is mediated by the chemokine receptor CC-CKR-5. Nature, 381, 667–673.

Ebenbichler, C. F., Roder, C., Vornhagen, R., Ratner, L., and Dierich, M. P. (1993). Cell surface proteins binding to recombinant soluble HIV-1 and HIV-2 transmembrane proteins. AIDS, 7, 489–495.

Ebenbichler, C. F., Stoiber, H., Schneider, R., Patsch, J. R., and Dierich, M. P. (1996). The human immunodeficiency virus type 1 transmembrane gp41 protein is a calcium-binding protein and interacts with the putative second-receptor molecules in a calcium-dependent manner. J. Virol., 70, 1723–1728.

Fass, D., Harrison, S. C., and Kim, P. S. (1996). Retrovirus envelope domain at 1.7 angstrom resolution. Nat. Struct. biol., 3, 465–9.

Fass, D., and Kim, P. S. (1995). Dissection of a retrovirus envelope protein reveals structural similarity to influenza hemagglutinin. Current Biology, 5(12), 1377–1383.

Feng, Y., Broder, C. C., Kennedy, P. E., and Berger, E. A. (1996). HIV-1 cofactor: functional cDNA cloning of a seven-transmembrane G protein-coupled receptor. Science, 272, 872–877.

Frangioni, J. V., and Neel, B. G. (1993). Solubilization and purification of enzymatically active glutathione S-transferase (pGEX) fusion proteins. Anal. Biochem., 210, 179–187.

Gallaher, W. R., Ball, J. M., Garry, R. F., Griffin, M. C., and Montelaro, R. C. (1989). A general model for the transmembrane proteins of HIV and other retroviruses. AIDS Res. Human Retroviruses, 5, 431–440.

Hopkins, N. (1993). High titers of retrovirus (vesicular stomatitis virus) pseudotyped, at last. Proc. Natl. Acad. Sci. USA, 90, 8759–8760.

Hunter, E., and Swanstrom, R. (1990). Retrovirus envelope glycoproteins. Curr. Top. Microbiol. Immunol., 157, 187–253.

Kasahara, N., Dozy, A. M., and Kan, Y. W. (1994). Tissue-specific targeting of retroviral vectors through ligand-receptor interactions. Science, 266, 1373–1376.

Lam, J. S., Reeves, M. E., Cowherd, R., Rosenberg, S. A., and Hwu, P. (1996). Improved gene transfer into human lymphocytes using retroviruses with the Gibbon Ape leukemia virus envelope. Human Gene Therapy, 7, 1415–1422.

Leboulch, P., Huang, G. M. S., Humphries, R. K., Oh, Y. H., Eaves, C. J., Tuan, D. Y. H., and London, I. M. (1994). Mutagenesis of retroviral vectors transducing human b-globin gene and b-globin locus control region derivatives results in stable transmission of an active transcriptional structure. The EMBO Journal, 13, 3065–3076.

Leboulch, P., Takekosh, K. J., Pawliuk, R., Humphries, R. K.,

London, I. M., Eaves, C. J., and Nagel, R. (1995). Progress towards the gene therapy of human b-globin gene disorders using retroviral vectors that transfer b-globin gene and b-locus control region derivatives. Sickle cell disease and thalassaemias: new trends in therapy, Y. Beuzard, B. Lubin, and J. Ross, eds., Colloque INSERM/John libbey Eurotext Ldt, 125–134.

Li, X., McDermott, B., Yuan, B., and Goff, S. P. (1996). Homomeric interaction between transmembrane proteins of moloney murine leukemia virus. J. Virol., 70(2), 1266–1270.

Li, X., Yuan, B., and Goff, S. P. (1997). Genetic analysis of interactions between Gag proteins of Rous Sarcoma virus. Journal of Virology, 71, 5624–5630.

Lu, M., Blacklow, S. C., and Kim, P. S. (1995). A trimeric structural domain of the HIV-1 transmembrane glycoprotein. Nat. Struct. Biol., 2, 1075–82.

Luban, J., and Goff, S. P. (1995). The yeast two-hybrid system for studing protein-protein interactions. Curr. Opinion in Biotechnology, 6, 59–64.

Mann, R., Mulligan, R. C., and Baltimore. (1983). Construction of a retrovirus packaging mutant and its use to produce helper-free defective retrovirus. cell, 33, 153–159.

Markowitz, D., Goff, S. P., and Bank, A. (1988a). Construction and use of a safe and efficient amphotropic packaging cell line. Virology, 167, 400–406.

Markowitz, D., Goff, S. P., and Bank, A. (1988b). A safe packaging line for gene transfer: separating viral genes on two different plasmids. J. Virol., 62(4), 1120–1124.

Marsh, M., and Helenius, A. (1989). Viral entry into animal cells. Adv. Virus Res., 36, 107–151.

Miller, A. D., Law, M.-F., and Verma, I. M. (1985). Generation of helper-free amphotropic retroviruses that transduce a dominant-acting methotrexate-resistant dihydrofolate reductase gene. Mol. Cell. Biol., 5, 431–437.

Mulligan, R. C. (1993). The basic science of gene therapy. Science, 260, 926–932.

Ory, D. S., Neugeboren, B. A., and Mulligan, R. (1996). A stable human-derived packaging cell line for production of high titer retrovirus/vesicular stomatitis virus G pseudotypes. Proc. Natl. Acad. Sci. USA, 93, 11400–11406.

Porter, C. D., Collins, M. K. L., Tailor, S. C., Parkar, M. H., Cosset, F.-L., Weiss, R. A., and Takeuchi, Y. (1996). Comparison of efficiency of infection of human gene therapy target cells via four different retroviral receptors. Human gene therapy, 7, 913–919.

Ragheb, J. A., Yu, H., Hofmann, T., and Anderson, W. F. (1995). The amphotropic and Ecotropic murine leukemia virus envelope TM subunits are equivalent mediators of direct membrane fusion: Implications for the role of the ecotropic envelope and receptor in syncytium formation and virla entry. J. Virol., 69(11), 7205–7215.

Sharma, S., Cantwell, M., Kipps, T. J., and Friedmann, T. (1996). Efficient infection of a human T-cell line and human primary peripheral blood leukocytes with a pseudotyped retrovirus vector. Proc. Natl. Acad. Sci. USA, 93, 11842–11847.

Sorge, J., Wright, D., Erdman, V. D., and Cutting, A. (1984). Amphotropic retrovirus system for human cell gene transfer. Mol. Cell. Biol., 4, 1730–1737.

Takekosh, K. J., Oh, Y. H., Westerman, K. W., London, I. M., and Leboulch, P. (1995). Retroviral transfer of a human b-globin/-globin hybrid gene linked to b locus control region hypersensitive site 2 aimed at the gene therapy of sickle cell disease. Proc. Natl. Acad. Sci. USA, 92, 3014–3018.

Wang, S., Beattie, G. M., Hayek, A., and Levine, F. (1996). Development of a VSV-G protein pseudotyped retroviral vector system expressing dominant oncogenes from a lacO-modified inducible LTR promoter. Gene, 182, 145–150.

Watanabe, S., and Temin, H. M. (1983). Construction of a cell line for avian reticuloendotheliosis virus cloning vectors. Mol. Cell. Biol., 3, 2241–2249.

White, J. (1992). Membrane fusion. Science, 258, 917–924.

SEQUENCE LISTING

<160> NUMBER OF SEQ ID NOS: 106

<210> SEQ ID NO 1
<211> LENGTH: 1536
<212> TYPE: DNA
<213> ORGANISM: murine

<400> SEQUENCE: 1

```
gaggtaccga cccttgacgt cggggtacta cctcatccct cgggcgtgat ggctacgggc      60
gcagatgtac gagacattct agaactcggg ggtccagagg gagatgccgc ctctgggacc     120
atcagcaaaa aggatattat caacccggac aagaaaaagt ccaagaagtc ctcagagacg     180
ctgaccttca agaggcctga gggcatgcat cgggaggtct atgctttgct ttactctgac     240
```

-continued

```
aaaaaggatg caccccccact gctgccagt gacactggtc gggggcatcg acagtgaag        300
gcgaaactgg ggtccaagaa ggttcgccct tggaaatgga tgccttttac taacccagct        360
cgaaaggacg gcgctatgtt tttccactgg cgacgagcgg cggaggaggg caaggactac        420
ccttttgcca ggttcaataa gacggtgcag gtgcccgtgt actcagagca ggagtaccaa        480
ctctcacttc atgatgacgc atggactaag gcagagactg accacctatt tgacctcagc        540
cgccgatttg atctgcgctt cgtagttatt cacgatcggt atgaccacca gcagttcaag        600
aagcgttctg tggaggacct gaaagagagg tactaccaca tttgtgccaa gcttgccaac        660
gtgagggctg tgccaggcac agatctcaag ataccagtgt ttgatgctgg gcatgagaga        720
cggcggaagg aacagctaga gcggctttac aaccgaaccc cagagcaggt ggcagaggag        780
gagtacctcc tacaggagct gcgtaagatt gaggcccgga aaaagagcg ggagaagcgc         840
agccaagacc tgcagaagct gattacagca gcagacacca ctgcagagca gcggcgcacg        900
gaacgcaagg ctcccaagaa gaagctaccc caaaagaagg aggctgagaa gccggctgtc        960
cctgagactg caggcatcaa gtttccagat tttaagtcgg caggtgtcac gctacggacg       1020
cagcggatga agctacccag ctatgtgggt cagaagaaga tcaaggcgct ggaacagatg       1080
ctgctggaac ttggtgtgga gctgagcccct acccccacag aggagctggt gcatatgttc       1140
aatgagttgc ggagcgacct ggtgttactt tacgagctca gcaggcctg tgccaactgt         1200
gaatatgagc tacagatgct gcggcaccgg cacgaggccc tggctcgggc aggagtgctg       1260
ggggcccctg ccgcagcagc agtgggacca accccggctt ctgctgagcc aacagtgtct       1320
gaatctggac ttggtctgga ccccaccaag gataccatca ttgatgtcgt gggtgcaccc       1380
ctcacaccca attcgcggaa acgacgggaa tcagcctcca gctcatcttc tgtgaagaaa       1440
gccaagaaac cataagggg catctgagtt ggtggtatgg tgtaaataga gctgttacat        1500
tgaaaaaaaa aaaaaaaaaa aaaaaaaaaa ctcgac                                  1536
```

<210> SEQ ID NO 2
<211> LENGTH: 483
<212> TYPE: PRT
<213> ORGANISM: murine

<400> SEQUENCE: 2

```
Glu Val Pro Thr Leu Asp Val Gly Val Leu Pro His Pro Ser Gly Val
 1               5                  10                  15

Met Ala Thr Gly Ala Asp Val Arg Asp Ile Leu Glu Leu Gly Gly Pro
            20                  25                  30

Glu Gly Asp Ala Ala Ser Gly Thr Ile Ser Lys Lys Asp Ile Ile Asn
        35                  40                  45

Pro Asp Lys Lys Lys Ser Lys Lys Ser Ser Glu Thr Leu Thr Phe Lys
    50                  55                  60

Arg Pro Glu Gly Met His Arg Glu Val Tyr Ala Leu Leu Tyr Ser Asp
65                  70                  75                  80

Lys Lys Asp Ala Pro Pro Leu Leu Pro Ser Asp Thr Gly Arg Gly His
                85                  90                  95

Arg Thr Val Lys Ala Lys Leu Gly Ser Lys Lys Val Arg Pro Trp Lys
            100                 105                 110

Trp Met Pro Phe Thr Asn Pro Ala Arg Lys Asp Gly Ala Met Phe Phe
        115                 120                 125

His Trp Arg Arg Ala Ala Glu Glu Gly Lys Asp Tyr Pro Phe Ala Arg
    130                 135                 140
```

```
Phe Asn Lys Thr Val Gln Val Pro Val Tyr Ser Glu Gln Glu Tyr Gln
145                 150                 155                 160

Leu Tyr Leu His Asp Asp Ala Trp Thr Lys Ala Glu Thr Asp His Leu
            165                 170                 175

Phe Asp Leu Ser Arg Arg Phe Asp Leu Arg Phe Val Val Ile His Asp
        180                 185                 190

Arg Tyr Asp His Gln Gln Phe Lys Lys Arg Ser Val Glu Asp Leu Lys
    195                 200                 205

Glu Arg Tyr Tyr His Ile Cys Ala Lys Leu Ala Asn Val Arg Ala Val
210                 215                 220

Pro Gly Thr Asp Leu Lys Ile Pro Val Phe Asp Ala Gly His Glu Arg
225                 230                 235                 240

Arg Arg Lys Glu Gln Leu Glu Arg Leu Tyr Asn Arg Thr Pro Glu Gln
                245                 250                 255

Val Ala Glu Glu Glu Tyr Leu Leu Gln Glu Leu Arg Lys Ile Glu Ala
            260                 265                 270

Arg Lys Lys Glu Glu Lys Arg Ser Gln Asp Leu Gln Lys Leu Ile Thr
        275                 280                 285

Ala Ala Asp Thr Thr Ala Glu Gln Arg Arg Thr Glu Arg Lys Ala Pro
    290                 295                 300

Lys Lys Lys Leu Pro Gln Lys Lys Glu Ala Lys Pro Ala Val Pro
305                 310                 315                 320

Glu Thr Ala Gly Ile Lys Phe Pro Asp Phe Lys Ser Ala Gly Val Thr
                325                 330                 335

Leu Arg Ser Gln Arg Met Lys Leu Pro Ser Ser Val Gly Gln Lys Lys
            340                 345                 350

Ile Lys Ala Leu Glu Gln Met Leu Leu Glu Leu Gly Val Glu Leu Ser
        355                 360                 365

Pro Thr Pro Thr Glu Glu Leu Val His Met Phe Asn Glu Leu Arg Ser
    370                 375                 380

Asp Leu Val Leu Leu Tyr Glu Leu Lys Gln Ala Cys Ala Asn Cys Glu
385                 390                 395                 400

Tyr Glu Leu Gln Met Leu Arg His Arg His Glu Ala Leu Ala Arg Ala
                405                 410                 415

Gly Val Leu Gly Ala Pro Ala Ala Ala Val Gly Pro Thr Pro Ala
            420                 425                 430

Ser Ala Glu Pro Thr Val Ser Glu Ser Gly Leu Gly Leu Asp Pro Thr
        435                 440                 445

Lys Asp Thr Ile Ile Asp Val Val Gly Ala Pro Leu Thr Pro Asn Ser
    450                 455                 460

Arg Lys Arg Arg Glu Ser Ala Ser Ser Ser Ser Val Lys Lys Ala
465                 470                 475                 480

Lys Lys Pro

<210> SEQ ID NO 3
<211> LENGTH: 15
<212> TYPE: PRT
<213> ORGANISM: murine

<400> SEQUENCE: 3

Arg Tyr Arg Pro Leu Thr Ser Gly Tyr Tyr Leu Ile Pro Arg Ala
  1               5                  10                  15

<210> SEQ ID NO 4
<211> LENGTH: 4
```

```
<212> TYPE: PRT
<213> ORGANISM: murine

<400> SEQUENCE: 4

Gly Thr Asp Pro
 1

<210> SEQ ID NO 5
<211> LENGTH: 1734
<212> TYPE: DNA
<213> ORGANISM: murine

<400> SEQUENCE: 5
cggaactggt cgggatgagt ggcggaggca ccgagacccc tgtagcgtgc gacgccgccc      60
agggcggcaa gaagcgggac tcactgggga ctccgggtgc ggcgcacctc attatcaagg     120
atcttggaga gattcattcc aggctgctgg atcacagacc agttacccaa ggtgaaatcc     180
gttactttgt aaaagaattt gaagaaaaac gtggccttcg agaattgcgc gttcttaaga     240
acttggagaa tacgatccag gaaacaaatg agtgcctgct tcccaaatgc agagagacca     300
tggagtgcgg cctgggggag accctgcaga gattgcaagc agctaacgac tccatctgca     360
gactccagca gagagaacag gaacggaaaa aggtgattaa tgactacttg acagctagtg     420
agaagcgtcg tctggtccag tgggaggagt tcgtgagcgg acagccgcag cgcagagctg     480
aggtggacga ggagcacaga agagccgtgg agaggctccg agagcagtat gcagcaatgg     540
agaaggacct ggccaagttt ccaccttttt aagactttga tctaaaagag acagatgaat     600
gaggaagtgc tttctcattc ccccaatcct cccaccaacc atgtagtctc tccttcaagc     660
ttagcagtac actcaggggc actcttaggt ctgaagagac acactgccgg agccagatac     720
atgtccagtg gaagaagcgt gcttctgcac ctaactgtgg tcatctgaag gagaggaggg     780
cggtggggca catttgctgc tggacagatt tgatcttttc attgattagc ttagagggct     840
gtgagtgtag atttcttcat tcattccacc aagggcaaat gtttgacctt gtggattaaa     900
tggcaggtat gacaacttcc catcacagca tcctgtgaca gagataccac agtgggcttt     960
gaacgcttgc ttggagacac caggttttgc agtgcaacac agtgccatgt ctttcacttt    1020
gtgacaagac attacatgac tggtagcctt gtagcactta atattttcat tttctaagct    1080
atgcttagga gaaaaaccaa atgtatttt gacttttcc tctccaagga ccatcatctc    1140
gcccatagag ctcaccttgc ctccgctcc atttcgctct gggccagcgc tccacggaac    1200
agtgtctgtg catgactcag ctgcgcagtg agtcggcagc agagtctgcc aagtccttcc    1260
caggccgtgt aagacgggct ctgggtgggc agaaagtgct cgcccacact gatgatgatg    1320
tatcagaggt aaaccctctt tgtcttagca tcctttctcc agcaggcttg tccggatgga    1380
acaccgctgt ctaccaccac tgtagtattt ctgtgcctgc acttagtcta aggaaggacc    1440
acatcaaacg tcatttgctg taaactaaac aaggtcacgc actcatttga gatgcatagc    1500
ctgtgcattt gaggtgtggg tgggtctttc tagtatttcc ttctcctcag taaagaaggg    1560
taaggcagag aaccccctaac tgtcgtgtta tctcagaatt ctcaatgcag acaattgaca    1620
atgcgtgcct gtgtaaatgt acgtaaatgt acggctgact gtgagagctt cgttcttggc    1680
tcatgctgaa gtgggattaa agctaataga agagatgaaa aaaaaaaaaa aaaa          1734

<210> SEQ ID NO 6
<211> LENGTH: 5
<212> TYPE: PRT
<213> ORGANISM: murine
```

```
<400> SEQUENCE: 6

Arg Asn Trp Ser Gly
 1               5

<210> SEQ ID NO 7
<211> LENGTH: 57
<212> TYPE: PRT
<213> ORGANISM: murine

<400> SEQUENCE: 7

Gly Thr Gly Arg Asp Glu Trp Arg Arg His Arg Asp Pro Cys Ser Val
 1               5                  10                  15

Arg Arg Arg Pro Gly Arg Gln Glu Ala Gly Leu Thr Gly Asp Ser Gly
                20                  25                  30

Cys Gly Ala Pro His Tyr Gln Gly Ser Trp Arg Asp Ser Phe Gln Ala
            35                  40                  45

Ala Gly Ser Gln Thr Ser Tyr Pro Arg
        50                  55

<210> SEQ ID NO 8
<211> LENGTH: 189
<212> TYPE: PRT
<213> ORGANISM: murine

<400> SEQUENCE: 8

Glu Leu Val Gly Met Ser Gly Gly Thr Glu Thr Pro Val Ala Cys
 1               5                  10                  15

Asp Ala Ala Gln Gly Gly Lys Lys Arg Asp Ser Leu Gly Thr Pro Gly
                20                  25                  30

Ala Ala His Leu Ile Ile Lys Asp Leu Gly Glu Ile His Ser Arg Leu
            35                  40                  45

Leu Asp His Arg Pro Val Thr Gln Gly Glu Ile Arg Tyr Phe Val Lys
        50                  55                  60

Glu Phe Glu Glu Lys Arg Gly Leu Arg Glu Leu Arg Val Leu Lys Asn
65                  70                  75                  80

Leu Glu Asn Thr Ile Gln Glu Thr Asn Glu Cys Leu Leu Pro Lys Cys
                85                  90                  95

Arg Glu Thr Met Glu Cys Gly Leu Gly Glu Thr Leu Gln Arg Leu Gln
                100                 105                 110

Ala Ala Asn Asp Ser Ile Cys Arg Leu Gln Gln Arg Glu Gln Glu Arg
            115                 120                 125

Lys Lys Val Ile Asn Asp Tyr Leu Thr Ala Ser Glu Lys Arg Arg Leu
        130                 135                 140

Val Gln Trp Glu Glu Phe Val Ser Gly Gln Pro Gln Arg Arg Ala Glu
145                 150                 155                 160

Val Asp Glu Glu His Arg Arg Ala Val Glu Arg Leu Arg Glu Gln Tyr
                165                 170                 175

Ala Ala Met Glu Lys Asp Leu Ala Lys Phe Ser Thr Phe
            180                 185

<210> SEQ ID NO 9
<211> LENGTH: 5
<212> TYPE: PRT
<213> ORGANISM: murine
```

```
<400> SEQUENCE: 9

Val Gly Gly Met Val
 1               5

<210> SEQ ID NO 10
<211> LENGTH: 5
<212> TYPE: PRT
<213> ORGANISM: murine

<400> SEQUENCE: 10

Ile Glu Leu Leu His
 1               5

<210> SEQ ID NO 11
<211> LENGTH: 11
<212> TYPE: PRT
<213> ORGANISM: murine

<400> SEQUENCE: 11

Lys Lys Lys Lys Lys Lys Lys Lys Lys Leu Asp
 1               5                  10

<210> SEQ ID NO 12
<211> LENGTH: 10
<212> TYPE: PRT
<213> ORGANISM: murine

<400> SEQUENCE: 12

Trp Leu Arg Ala Gln Met Tyr Glu Thr Phe
 1               5                  10

<210> SEQ ID NO 13
<211> LENGTH: 33
<212> TYPE: PRT
<213> ORGANISM: murine

<400> SEQUENCE: 13

Asn Ser Gly Val Gln Arg Glu Met Pro Pro Leu Gly Pro Ser Ala Lys
 1               5                  10                  15

Arg Ile Leu Ser Thr Arg Thr Arg Lys Ser Pro Arg Ser Pro Gln Arg
                20                  25                  30

Arg

<210> SEQ ID NO 14
<211> LENGTH: 36
<212> TYPE: PRT
<213> ORGANISM: murine

<400> SEQUENCE: 14

Pro Ser Arg Leu Arg Ala Cys Ile Gly Arg Ser Met Leu Cys Phe Thr
 1               5                  10                  15

Leu Thr Lys Arg Met His Pro His Cys Cys Pro Val Thr Leu Val Gly
                20                  25                  30

Gly Ile Gly Gln
                35

<210> SEQ ID NO 15
<211> LENGTH: 88
<212> TYPE: PRT
<213> ORGANISM: murine

<400> SEQUENCE: 15
```

```
Arg Arg Asn Trp Gly Pro Arg Phe Ala Leu Gly Asn Gly Cys Leu
 1               5                  10                  15

Leu Leu Thr Gln Leu Glu Arg Thr Ala Leu Cys Phe Ser Thr Gly Asp
                20                  25                  30

Glu Arg Arg Arg Ala Arg Thr Leu Leu Pro Gly Ser Ile Arg
            35                  40                  45

Arg Cys Arg Cys Pro Cys Thr Gln Ser Arg Ser Thr Asn Ser Thr Phe
        50                  55                  60

Met Met Thr His Gly Leu Arg Gln Arg Leu Thr Thr Tyr Leu Thr Ser
 65                 70                  75                  80

Ala Ala Asp Leu Ile Cys Ala Ser
                85
```

<210> SEQ ID NO 16
<211> LENGTH: 18
<212> TYPE: PRT
<213> ORGANISM: murine
<400> SEQUENCE: 16

```
Leu Phe Thr Ile Gly Met Thr Thr Ser Ser Arg Ser Val Leu Trp
 1               5                  10                  15

Arg Thr
```

<210> SEQ ID NO 17
<211> LENGTH: 13
<212> TYPE: PRT
<213> ORGANISM: murine
<400> SEQUENCE: 17

```
Lys Arg Gly Thr Thr Thr Phe Val Pro Ser Leu Pro Thr
 1               5                  10
```

<210> SEQ ID NO 18
<211> LENGTH: 24
<212> TYPE: PRT
<213> ORGANISM: murine
<400> SEQUENCE: 18

```
Gly Leu Cys Gln Ala Gln Ile Ser Arg Tyr Gln Cys Leu Met Leu Gly
 1               5                  10                  15

Met Arg Asp Gly Gly Arg Asn Ser
                20
```

<210> SEQ ID NO 19
<211> LENGTH: 40
<212> TYPE: PRT
<213> ORGANISM: murine
<400> SEQUENCE: 19

```
Ser Gly Phe Thr Thr Glu Pro Gln Ser Arg Trp Gln Arg Arg Ser Thr
 1               5                  10                  15

Ser Tyr Arg Ser Cys Val Arg Leu Arg Pro Gly Lys Lys Ser Gly Arg
                20                  25                  30

Ser Ala Ala Lys Thr Cys Arg Ser
            35                  40
```

<210> SEQ ID NO 20
<211> LENGTH: 54
<212> TYPE: PRT
<213> ORGANISM: murine -continued

<400> SEQUENCE: 20

Leu Gln Gln Gln Thr Pro Leu Gln Ser Ser Gly Ala Arg Asn Ala Arg
1               5                   10                  15

Leu Pro Arg Arg Ser Tyr Pro Lys Arg Arg Leu Arg Ser Arg Leu
            20                  25                  30

Ser Leu Arg Leu Gln Ala Ser Ser Phe Gln Ile Leu Ser Arg Gln Val
            35                  40                  45

Ser Arg Gly Ala Ser Gly
        50

<210> SEQ ID NO 21
<211> LENGTH: 24
<212> TYPE: PRT
<213> ORGANISM: murine

<400> SEQUENCE: 21

Ser Tyr Pro Ala Leu Trp Val Arg Arg Ser Arg Arg Trp Asn Arg
1               5                   10                  15

Cys Cys Trp Asn Leu Val Trp Ser
            20

<210> SEQ ID NO 22
<211> LENGTH: 109
<212> TYPE: PRT
<213> ORGANISM: murine

<400> SEQUENCE: 22

Ala Leu Pro Pro Gln Arg Ser Trp Cys Ile Cys Ser Met Ser Cys Gly
1               5                   10                  15

Ala Thr Trp Cys Tyr Phe Thr Ser Ser Ser Arg Pro Val Pro Thr Val
            20                  25                  30

Asn Met Ser Tyr Arg Cys Cys Gly Thr Gly Thr Arg Pro Trp Leu Gly
            35                  40                  45

Gln Glu Cys Trp Gly Pro Leu Pro Gln Gln Trp Asp Gln Pro Arg
        50                  55                  60

Leu Leu Leu Ser Gln Gln Cys Leu Asn Leu Asp Leu Val Trp Thr Pro
65              70                  75                  80

Pro Arg Ile Pro Ser Leu Met Ser Trp Val His Pro Ser His Pro Ile
                85                  90                  95

Arg Gly Asn Asp Gly Asn Gln Pro Pro Ala His Leu Leu
            100                 105

<210> SEQ ID NO 23
<211> LENGTH: 17
<212> TYPE: PRT
<213> ORGANISM: murine

<400> SEQUENCE: 23

Arg Lys Pro Arg Asn His Lys Gly Pro Ser Glu Leu Val Val Trp Cys
1               5                   10                  15

Lys

<210> SEQ ID NO 24
<211> LENGTH: 15
<212> TYPE: PRT
<213> ORGANISM: murine

<400> SEQUENCE: 24

Ser Cys Tyr Ile Glu Lys Lys Lys Lys Lys Lys Asn Ser
1               5                  10                 15

<210> SEQ ID NO 25
<211> LENGTH: 60
<212> TYPE: PRT
<213> ORGANISM: murine

<400> SEQUENCE: 25

Arg Arg Gly Thr Thr Ser Ser Leu Gly Arg Asp Gly Tyr Gly Arg Arg
1               5                  10                 15

Cys Thr Arg His Ser Arg Thr Arg Gly Ser Arg Gly Arg Cys Arg Leu
            20                  25                  30

Trp Asp His Gln Gln Lys Gly Tyr Tyr Gln Pro Gly Gln Glu Lys Val
        35                  40                  45

Gln Glu Val Leu Arg Asp Ala Asp Leu Gln Glu Ala
    50                  55                  60

<210> SEQ ID NO 26
<211> LENGTH: 12
<212> TYPE: PRT
<213> ORGANISM: murine

<400> SEQUENCE: 26

Gly His Ala Ser Gly Gly Leu Cys Phe Ala Leu Leu
1               5                  10

<210> SEQ ID NO 27
<211> LENGTH: 10
<212> TYPE: PRT
<213> ORGANISM: murine

<400> SEQUENCE: 27

Gln Lys Gly Cys Thr Pro Thr Ala Ala Gln
1               5                  10

<210> SEQ ID NO 28
<211> LENGTH: 26
<212> TYPE: PRT
<213> ORGANISM: murine

<400> SEQUENCE: 28

His Trp Ser Gly Ala Ser Asp Ser Glu Gly Glu Thr Gly Val Gln Glu
1               5                  10                 15

Gly Ser Pro Leu Glu Met Asp Ala Phe Tyr
            20                  25

<210> SEQ ID NO 29
<211> LENGTH: 28
<212> TYPE: PRT
<213> ORGANISM: murine

<400> SEQUENCE: 29

Pro Ser Ser Lys Gly Arg Arg Tyr Val Phe Pro Leu Ala Thr Ser Gly
1               5                  10                 15

Gly Gly Gly Gln Gly Leu Pro Phe Cys Gln Val Gln
            20                  25

<210> SEQ ID NO 30
<211> LENGTH: 17
<212> TYPE: PRT
<213> ORGANISM: murine

```
<400> SEQUENCE: 30

Asp Gly Ala Gly Ala Arg Val Leu Arg Ala Gly Val Pro Thr Leu Pro
 1               5                  10                  15
Ser

<210> SEQ ID NO 31
<211> LENGTH: 5
<212> TYPE: PRT
<213> ORGANISM: murine

<400> SEQUENCE: 31

Pro Gln Pro Pro Ile
 1               5

<210> SEQ ID NO 32
<211> LENGTH: 10
<212> TYPE: PRT
<213> ORGANISM: murine

<400> SEQUENCE: 32

Ser Ala Leu Arg Ser Tyr Ser Arg Ser Val
 1               5                  10

<210> SEQ ID NO 33
<211> LENGTH: 60
<212> TYPE: PRT
<213> ORGANISM: murine

<400> SEQUENCE: 33

Arg Arg Gly Thr Thr Ser Ser Leu Gly Arg Asp Gly Tyr Gly Arg Arg
 1               5                  10                  15

Cys Thr Arg His Ser Arg Thr Arg Gly Ser Arg Gly Arg Cys Arg Leu
                20                  25                  30

Trp Asp His Gln Gln Lys Gly Tyr Tyr Gln Pro Gly Gln Glu Lys Val
            35                  40                  45

Gln Glu Val Leu Arg Asp Ala Asp Leu Gln Glu Ala
        50                  55                  60

<210> SEQ ID NO 34
<211> LENGTH: 29
<212> TYPE: PRT
<213> ORGANISM: murine

<400> SEQUENCE: 34

Glu Thr Ala Glu Gly Thr Ala Arg Ala Ala Leu Gln Pro Asn Pro Arg
 1               5                  10                  15

Ala Gly Gly Arg Gly Gly Val Pro Pro Thr Gly Ala Ala
                20                  25

<210> SEQ ID NO 35
<211> LENGTH: 44
<212> TYPE: PRT
<213> ORGANISM: murine

<400> SEQUENCE: 35

Gly Pro Glu Lys Arg Ala Gly Glu Ala Gln Pro Arg Pro Ala Glu Ala
 1               5                  10                  15

Asp Tyr Ser Ser Arg His His Cys Arg Ala Ala Ala His Gly Thr Gln
                20                  25                  30

Gly Ser Gln Glu Glu Ala Thr Pro Lys Glu Gly Gly
            35                  40
```

<210> SEQ ID NO 36
<211> LENGTH: 5
<212> TYPE: PRT
<213> ORGANISM: murine

<400> SEQUENCE: 36

Glu Ala Gly Cys Pro
 1               5

<210> SEQ ID NO 37
<211> LENGTH: 9
<212> TYPE: PRT
<213> ORGANISM: murine

<400> SEQUENCE: 37

Asp Cys Arg His Gln Val Ser Arg Phe
 1               5

<210> SEQ ID NO 38
<211> LENGTH: 49
<212> TYPE: PRT
<213> ORGANISM: murine

<400> SEQUENCE: 38

Val Gly Arg Cys His Ala Thr Glu Pro Ala Asp Glu Ala Thr Gln Leu
 1               5                  10                  15

Cys Gly Ser Glu Glu Asp Gln Gly Ala Gly Thr Asp Ala Ala Gly Thr
                20                  25                  30

Trp Cys Gly Ala Glu Pro Tyr Pro His Arg Gly Ala Gly Ala Tyr Val
            35                  40                  45

Gln

<210> SEQ ID NO 39
<211> LENGTH: 18
<212> TYPE: PRT
<213> ORGANISM: murine

<400> SEQUENCE: 39

Val Ala Glu Arg Pro Gly Val Thr Leu Arg Ala Gln Ala Gly Leu Cys
 1               5                  10                  15

Gln Leu

<210> SEQ ID NO 40
<211> LENGTH: 32
<212> TYPE: PRT
<213> ORGANISM: murine

<400> SEQUENCE: 40

Ala Thr Asp Ala Ala Ala Pro Arg Gly Pro Gly Ser Gly Arg Ser
 1               5                  10                  15

Ala Gly Gly Pro Cys Arg Ser Ser Ser Gly Thr Asn Pro Gly Phe Cys
                20                  25                  30

<210> SEQ ID NO 41
<211> LENGTH: 4
<212> TYPE: PRT
<213> ORGANISM: murine

<400> SEQUENCE: 41

Ala Asn Ser Val
 1

<210> SEQ ID NO 42
<211> LENGTH: 13
<212> TYPE: PRT
<213> ORGANISM: murine

<400> SEQUENCE: 42

Ile Trp Thr Trp Ser Gly Pro His Gln Gly Tyr His His
 1               5                  10

<210> SEQ ID NO 43
<211> LENGTH: 57
<212> TYPE: PRT
<213> ORGANISM: murine

<400> SEQUENCE: 43

Cys Arg Gly Cys Thr Pro His Thr Gln Phe Ala Glu Thr Thr Gly Ile
 1               5                  10                  15

Ser Leu Gln Leu Ile Phe Cys Glu Glu Ser Gln Glu Thr Ile Arg Gly
            20                  25                  30

His Leu Ser Trp Trp Tyr Gly Val Asn Arg Ala Val Thr Leu Lys Lys
        35                  40                  45

Lys Lys Lys Lys Lys Lys Thr Arg
    50                  55

<210> SEQ ID NO 44
<211> LENGTH: 8
<212> TYPE: PRT
<213> ORGANISM: murine

<400> SEQUENCE: 44

Val Ala Glu Ala Pro Arg Pro Leu
 1               5

<210> SEQ ID NO 45
<211> LENGTH: 48
<212> TYPE: PRT
<213> ORGANISM: murine

<400> SEQUENCE: 45

Arg Ala Thr Pro Pro Arg Ala Arg Ser Gly Thr His Trp Gly Leu
 1               5                  10                  15

Arg Val Arg Arg Thr Ser Leu Ser Arg Ile Leu Glu Arg Phe Ile Pro
            20                  25                  30

Gly Cys Trp Ile Thr Asp Gln Leu Pro Lys Val Lys Ser Val Thr Leu
        35                  40                  45

<210> SEQ ID NO 46
<211> LENGTH: 67
<212> TYPE: PRT
<213> ORGANISM: murine

<400> SEQUENCE: 46

Lys Asn Leu Lys Lys Asn Val Ala Phe Glu Asn Cys Ala Phe Leu Arg
 1               5                  10                  15

Thr Trp Arg Ile Arg Ser Arg Lys Gln Met Ser Ala Cys Phe Pro Asn
            20                  25                  30

Ala Glu Arg Pro Trp Ser Ala Ala Trp Gly Arg Pro Cys Arg Asp Cys
        35                  40                  45

Lys Gln Leu Thr Thr Pro Ser Ala Asp Ser Ser Arg Glu Asn Arg Asn
    50                  55                  60

Gly Lys Arg
 65

<210> SEQ ID NO 47
<211> LENGTH: 4
<212> TYPE: PRT
<213> ORGANISM: murine

<400> SEQUENCE: 47

Leu Met Thr Thr
 1

<210> SEQ ID NO 48
<211> LENGTH: 14
<212> TYPE: PRT
<213> ORGANISM: murine

<400> SEQUENCE: 48

Gln Leu Val Arg Ser Val Val Trp Ser Ser Gly Arg Ser Ser
 1               5                  10

<210> SEQ ID NO 49
<211> LENGTH: 42
<212> TYPE: PRT
<213> ORGANISM: murine

<400> SEQUENCE: 49

Ala Asp Ser Arg Ser Ala Glu Leu Arg Trp Thr Arg Ser Thr Glu Glu
 1               5                  10                  15

Pro Trp Arg Gly Ser Glu Ser Ser Met Gln Gln Trp Arg Arg Thr Trp
                20                  25                  30

Pro Ser Phe Pro Pro Phe Lys Thr Leu Ile
            35                  40

<210> SEQ ID NO 50
<211> LENGTH: 59
<212> TYPE: PRT
<213> ORGANISM: murine

<400> SEQUENCE: 50

Lys Arg Gln Met Asn Glu Glu Val Leu Ser His Ser Pro Asn Pro Thr
 1               5                  10                  15

Asn His Val Val Ser Pro Ser Leu Ala Val His Ser Gly Ala Leu
                20                  25                  30

Leu Gly Leu Lys Arg Asp Thr Ala Gly Ala Arg Tyr Met Ser Ser Gly
            35                  40                  45

Arg Ser Val Leu Leu His Leu Thr Val Val Ile
         50                  55

<210> SEQ ID NO 51
<211> LENGTH: 14
<212> TYPE: PRT
<213> ORGANISM: murine

<400> SEQUENCE: 51

Arg Arg Gly Gly Arg Trp Gly Thr Phe Ala Ala Gly Gln Ile
 1               5                  10

<210> SEQ ID NO 52
<211> LENGTH: 25
<212> TYPE: PRT
<213> ORGANISM: murine

```
<400> SEQUENCE: 52

Arg Ala Val Ser Val Asp Phe Phe Ile His Ser Thr Lys Gly Lys Cys
 1               5                  10                  15

Leu Thr Leu Trp Ile Lys Trp Gln Val
                20                  25

<210> SEQ ID NO 53
<211> LENGTH: 54
<212> TYPE: PRT
<213> ORGANISM: murine

<400> SEQUENCE: 53

Gln Leu Pro Ile Thr Ala Ser Cys Asp Arg Asp Thr Thr Val Gly Phe
 1               5                  10                  15

Glu Arg Leu Leu Gly Asp Thr Arg Phe Cys Ser Ala Thr Gln Cys His
                20                  25                  30

Val Phe His Phe Val Thr Arg His Tyr Met Thr Gly Ser Leu Val Ala
            35                  40                  45

Leu Asn Ile Phe Ile Phe
        50

<210> SEQ ID NO 54
<211> LENGTH: 45
<212> TYPE: PRT
<213> ORGANISM: murine

<400> SEQUENCE: 54

Ala Met Leu Arg Arg Lys Thr Lys Met Tyr Phe Asp Phe Phe Leu Ser
 1               5                  10                  15

Lys Asp His His Leu Ala His Arg Ala His Leu Ala Leu Arg Ser Ile
                20                  25                  30

Ser Leu Trp Ala Ser Ala Pro Arg Asn Ser Val Cys Ala
            35                  40                  45

<210> SEQ ID NO 55
<211> LENGTH: 18
<212> TYPE: PRT
<213> ORGANISM: murine

<400> SEQUENCE: 55

Leu Ser Cys Ala Val Ser Arg Gln Gln Ser Leu Pro Ser Pro Ser Gln
 1               5                  10                  15

Ala Val

<210> SEQ ID NO 56
<211> LENGTH: 19
<212> TYPE: PRT
<213> ORGANISM: murine

<400> SEQUENCE: 56

Asp Gly Leu Trp Val Gly Arg Lys Cys Ser Pro Thr Leu Met Met Met
 1               5                  10                  15

Tyr Gln Arg

<210> SEQ ID NO 57
<211> LENGTH: 32
<212> TYPE: PRT
<213> ORGANISM: murine

<400> SEQUENCE: 57
```

Thr Leu Phe Val Leu Ala Ser Phe Leu Gln Gln Ala Cys Pro Asp Gly
1               5                   10                  15

Thr Pro Leu Ser Thr Thr Thr Val Phe Leu Cys Leu His Leu Val
            20                  25                  30

<210> SEQ ID NO 58
<211> LENGTH: 26
<212> TYPE: PRT
<213> ORGANISM: murine

<400> SEQUENCE: 58

Gly Arg Thr Thr Ser Asn Val Ile Cys Cys Lys Leu Asn Lys Val Thr
1               5                   10                  15

His Ser Phe Glu Met His Ser Leu Cys Ile
            20                  25

<210> SEQ ID NO 59
<211> LENGTH: 6
<212> TYPE: PRT
<213> ORGANISM: murine

<400> SEQUENCE: 59

Gly Val Gly Gly Ser Phe
1               5

<210> SEQ ID NO 60
<211> LENGTH: 9
<212> TYPE: PRT
<213> ORGANISM: murine

<400> SEQUENCE: 60

Tyr Phe Leu Leu Leu Ser Lys Glu Gly
1               5

<210> SEQ ID NO 61
<211> LENGTH: 41
<212> TYPE: PRT
<213> ORGANISM: murine

<400> SEQUENCE: 61

Gly Arg Glu Pro Leu Thr Val Val Leu Ser Gln Asn Ser Gln Cys Arg
1               5                   10                  15

Gln Leu Thr Met Arg Ala Cys Val Asn Val Arg Lys Cys Thr Ala Asp
            20                  25                  30

Cys Glu Ser Phe Val Leu Gly Ser Cys
            35                  40

<210> SEQ ID NO 62
<211> LENGTH: 15
<212> TYPE: PRT
<213> ORGANISM: murine

<400> SEQUENCE: 62

Ser Gly Ile Lys Ala Asn Arg Arg Asp Glu Lys Lys Lys Lys
1               5                   10                  15

<210> SEQ ID NO 63
<211> LENGTH: 8
<212> TYPE: PRT
<213> ORGANISM: murine

<400> SEQUENCE: 63

Asn Pro Leu Leu Cys Lys Arg Ile
  1               5

<210> SEQ ID NO 64
<211> LENGTH: 11
<212> TYPE: PRT
<213> ORGANISM: murine

<400> SEQUENCE: 64

Arg Lys Thr Trp Pro Ser Arg Ile Ala Arg Ser
  1               5                  10

<210> SEQ ID NO 65
<211> LENGTH: 10
<212> TYPE: PRT
<213> ORGANISM: murine

<400> SEQUENCE: 65

Glu Leu Gly Glu Tyr Asp Pro Gly Asn Lys
  1               5                  10

<210> SEQ ID NO 66
<211> LENGTH: 24
<212> TYPE: PRT
<213> ORGANISM: murine

<400> SEQUENCE: 66

Val Pro Ala Ser Gln Met Gln Arg Asp His Gly Val Arg Pro Gly Gly
  1               5                  10                  15

Asp Pro Ala Glu Ile Ala Ser Ser
             20

<210> SEQ ID NO 67
<211> LENGTH: 16
<212> TYPE: PRT
<213> ORGANISM: murine

<400> SEQUENCE: 67

Arg Leu His Leu Gln Thr Pro Ala Glu Thr Gly Thr Glu Lys Gly Asp
  1               5                  10                  15

<210> SEQ ID NO 68
<211> LENGTH: 4
<212> TYPE: PRT
<213> ORGANISM: murine

<400> SEQUENCE: 68

Leu Leu Asp Ser
  1

<210> SEQ ID NO 69
<211> LENGTH: 19
<212> TYPE: PRT
<213> ORGANISM: murine

<400> SEQUENCE: 69

Glu Ala Ser Ser Gly Pro Val Gly Gly Val Arg Glu Arg Thr Ala Ala
  1               5                  10                  15

Ala Gln Ser

<210> SEQ ID NO 70
<211> LENGTH: 32
<212> TYPE: PRT
<213> ORGANISM: murine

<400> SEQUENCE: 70

Gly Gly Arg Gly Ala Gln Lys Ser Arg Gly Glu Ala Pro Arg Ala Val
1               5                   10                  15

Cys Ser Asn Gly Glu Gly Pro Gly Gln Val Phe His Leu Leu Arg Leu
            20                  25                  30

<210> SEQ ID NO 71
<211> LENGTH: 5
<212> TYPE: PRT
<213> ORGANISM: murine

<400> SEQUENCE: 71

Ser Lys Arg Asp Arg
1               5

<210> SEQ ID NO 72
<211> LENGTH: 15
<212> TYPE: PRT
<213> ORGANISM: murine

<400> SEQUENCE: 72

Met Arg Lys Cys Phe Leu Ile Pro Pro Ile Leu Pro Pro Thr Met
1               5                   10                  15

<210> SEQ ID NO 73
<211> LENGTH: 5
<212> TYPE: PRT
<213> ORGANISM: murine

<400> SEQUENCE: 73

Ser Leu Leu Gln Ala
1               5

<210> SEQ ID NO 74
<211> LENGTH: 7
<212> TYPE: PRT
<213> ORGANISM: murine

<400> SEQUENCE: 74

Gln Tyr Thr Gln Gly His Ser
1               5

<210> SEQ ID NO 75
<211> LENGTH: 19
<212> TYPE: PRT
<213> ORGANISM: murine

<400> SEQUENCE: 75

Arg Glu Thr Leu Pro Glu Pro Asp Thr Cys Pro Val Glu Glu Ala Cys
1               5                   10                  15

Phe Cys Thr

<210> SEQ ID NO 76
<211> LENGTH: 24
<212> TYPE: PRT
<213> ORGANISM: murine

<400> SEQUENCE: 76

Leu Trp Ser Ser Glu Gly Glu Glu Gly Gly Ala His Leu Leu Leu
1               5                   10                  15

Asp Arg Phe Asp Leu Phe Ile Asp
            20

```
<210> SEQ ID NO 77
<211> LENGTH: 4
<212> TYPE: PRT
<213> ORGANISM: murine

<400> SEQUENCE: 77

Leu Arg Gly Leu
 1

<210> SEQ ID NO 78
<211> LENGTH: 11
<212> TYPE: PRT
<213> ORGANISM: murine

<400> SEQUENCE: 78

Ile Ser Ser Phe Ile Pro Pro Arg Ala Asn Val
 1               5                  10

<210> SEQ ID NO 79
<211> LENGTH: 45
<212> TYPE: PRT
<213> ORGANISM: murine

<400> SEQUENCE: 79

Pro Cys Gly Leu Asn Gly Arg Tyr Asp Asn Phe Pro Ser Gln His Pro
 1               5                  10                  15

Val Thr Glu Ile Pro Gln Trp Ala Leu Asn Ala Cys Leu Glu Thr Pro
             20                  25                  30

Gly Phe Ala Val Gln His Ser Ala Met Ser Phe Thr Leu
         35                  40                  45

<210> SEQ ID NO 80
<211> LENGTH: 4
<212> TYPE: PRT
<213> ORGANISM: murine

<400> SEQUENCE: 80

Gln Asp Ile Thr
 1

<210> SEQ ID NO 81
<211> LENGTH: 4
<212> TYPE: PRT
<213> ORGANISM: murine

<400> SEQUENCE: 81

Leu Val Ala Leu
 1

<210> SEQ ID NO 82
<211> LENGTH: 58
<212> TYPE: PRT
<213> ORGANISM: murine

<400> SEQUENCE: 82

His Leu Ile Phe Ser Phe Ser Lys Leu Cys Leu Gly Glu Lys Pro Lys
 1               5                  10                  15

Cys Ile Leu Thr Phe Ser Ser Pro Arg Thr Ile Ile Ser Pro Ile Glu
             20                  25                  30

Leu Thr Leu Leu Ser Ala Pro Phe Arg Ser Gly Pro Ala Leu His Gly
         35                  40                  45
```

-continued

Thr Val Ser Val His Asp Ser Ala Ala Gln
            50                  55

<210> SEQ ID NO 83
<211> LENGTH: 26
<212> TYPE: PRT
<213> ORGANISM: murine

<400> SEQUENCE: 83

Val Gly Ser Arg Val Cys Gln Val Leu Pro Arg Pro Cys Lys Thr Gly
 1               5                  10                  15

Ser Gly Trp Ala Glu Ser Ala Arg Pro His
            20                  25

<210> SEQ ID NO 84
<211> LENGTH: 9
<212> TYPE: PRT
<213> ORGANISM: murine

<400> SEQUENCE: 84

Cys Ile Arg Gly Lys Pro Ser Leu Ser
 1               5

<210> SEQ ID NO 85
<211> LENGTH: 6
<212> TYPE: PRT
<213> ORGANISM: murine

<400> SEQUENCE: 85

Tyr Phe Cys Ala Cys Thr
 1               5

<210> SEQ ID NO 86
<211> LENGTH: 18
<212> TYPE: PRT
<213> ORGANISM: murine

<400> SEQUENCE: 86

His Pro Phe Ser Ser Arg Leu Val Arg Met Glu His Arg Cys Leu Pro
 1               5                  10                  15

Pro Leu

<210> SEQ ID NO 87
<211> LENGTH: 13
<212> TYPE: PRT
<213> ORGANISM: murine

<400> SEQUENCE: 87

Ser Lys Glu Gly Pro His Gln Thr Ser Phe Ala Val Asn
 1               5                  10

<210> SEQ ID NO 88
<211> LENGTH: 36
<212> TYPE: PRT
<213> ORGANISM: murine

<400> SEQUENCE: 88

Thr Arg Ser Arg Thr His Leu Arg Cys Ile Ala Cys Ala Phe Glu Val
 1               5                  10                  15

Trp Val Gly Leu Ser Ser Ile Ser Phe Ser Ser Val Lys Lys Gly Lys
                20                  25                  30

Ala Glu Asn Pro
            35

<210> SEQ ID NO 89
<211> LENGTH: 12
<212> TYPE: PRT
<213> ORGANISM: murine

<400> SEQUENCE: 89

Leu Ser Cys Tyr Leu Arg Ile Leu Asn Ala Asp Asn
1               5                   10

<210> SEQ ID NO 90
<211> LENGTH: 5
<212> TYPE: PRT
<213> ORGANISM: murine

<400> SEQUENCE: 90

Gln Cys Val Pro Val
1               5

<210> SEQ ID NO 91
<211> LENGTH: 32
<212> TYPE: PRT
<213> ORGANISM: murine

<400> SEQUENCE: 91

Met Tyr Val Asn Val Arg Leu Thr Val Arg Ala Ser Phe Leu Ala His
1               5                   10                  15

Ala Glu Val Gly Leu Lys Leu Ile Glu Glu Met Lys Lys Lys Lys Lys
                20                  25                  30

<210> SEQ ID NO 92
<211> LENGTH: 9
<212> TYPE: PRT
<213> ORGANISM: murine

<400> SEQUENCE: 92

Asp Phe Asp Leu Lys Glu Thr Asp Glu
1               5

<210> SEQ ID NO 93
<211> LENGTH: 98
<212> TYPE: PRT
<213> ORGANISM: murine

<400> SEQUENCE: 93

Gly Ser Ala Phe Ser Phe Pro Gln Ser Ser His Gln Pro Cys Ser Leu
1               5                   10                  15

Ser Phe Lys Leu Ser Ser Thr Leu Arg Gly Thr Leu Arg Ser Glu Glu
                20                  25                  30

Arg His Cys Arg Ser Gln Ile His Val Gln Trp Lys Lys Arg Ala Ser
                35                  40                  45

Ala Pro Asn Cys Gly His Leu Lys Glu Arg Arg Ala Val Gly His Ile
        50                  55                  60

Cys Cys Trp Thr Asp Leu Ile Phe Ser Leu Ile Ser Leu Glu Gly Cys
65                  70                  75                  80

Glu Cys Arg Phe Leu His Ser Phe His Gln Gly Gln Met Phe Asp Leu
                85                  90                  95

Val Asp

<210> SEQ ID NO 94
<211> LENGTH: 12

```
<212> TYPE: PRT
<213> ORGANISM: murine

<400> SEQUENCE: 94

Met Ala Gly Met Thr Thr Ser His His Ser Ile Leu
 1               5                  10

<210> SEQ ID NO 95
<211> LENGTH: 7
<212> TYPE: PRT
<213> ORGANISM: murine

<400> SEQUENCE: 95

Gln Arg Tyr His Ser Gly Leu
 1               5

<210> SEQ ID NO 96
<211> LENGTH: 27
<212> TYPE: PRT
<213> ORGANISM: murine

<400> SEQUENCE: 96

Thr Leu Ala Trp Arg His Gln Val Leu Gln Cys Asn Thr Val Pro Cys
 1               5                  10                  15

Leu Ser Leu Cys Asp Lys Thr Leu His Asp Trp
                20                  25

<210> SEQ ID NO 97
<211> LENGTH: 4
<212> TYPE: PRT
<213> ORGANISM: murine

<400> SEQUENCE: 97

Pro Cys Ser Thr
 1

<210> SEQ ID NO 98
<211> LENGTH: 8
<212> TYPE: PRT
<213> ORGANISM: murine

<400> SEQUENCE: 98

Tyr Phe His Phe Leu Ser Tyr Ala
 1               5

<210> SEQ ID NO 99
<211> LENGTH: 7
<212> TYPE: PRT
<213> ORGANISM: murine

<400> SEQUENCE: 99

Glu Lys Asn Gln Asn Val Phe
 1               5

<210> SEQ ID NO 100
<211> LENGTH: 11
<212> TYPE: PRT
<213> ORGANISM: murine

<400> SEQUENCE: 100

Leu Phe Pro Leu Gln Gly Pro Ser Ser Arg Pro
 1               5                  10

<210> SEQ ID NO 101
```

```
<211> LENGTH: 104
<212> TYPE: PRT
<213> ORGANISM: murine

<400> SEQUENCE: 101
```

Ser Ser Pro Cys Ser Pro Leu His Phe Ala Leu Gly Gln Arg Ser Thr
 1               5                  10                  15

Glu Gln Cys Leu Cys Met Thr Gln Leu Arg Ser Glu Ser Ala Ala Glu
            20                  25                  30

Ser Ala Lys Ser Phe Pro Gly Arg Val Arg Arg Ala Leu Gly Gly Gln
        35                  40                  45

Lys Val Leu Ala His Thr Asp Asp Val Ser Glu Val Asn Pro Leu
 50                  55                  60

Cys Leu Ser Ile Leu Ser Pro Ala Gly Leu Ser Gly Trp Asn Thr Ala
 65                  70                  75                  80

Val Tyr His His Cys Ser Ile Ser Val Pro Ala Leu Ser Leu Arg Lys
                85                  90                  95

Asp His Ile Lys Arg His Leu Leu
            100

```
<210> SEQ ID NO 102
<211> LENGTH: 8
<212> TYPE: PRT
<213> ORGANISM: murine

<400> SEQUENCE: 102
```

Thr Lys Gln Gly His Ala Leu Ile
 1               5

```
<210> SEQ ID NO 103
<211> LENGTH: 17
<212> TYPE: PRT
<213> ORGANISM: murine

<400> SEQUENCE: 103
```

Pro Val His Leu Arg Cys Gly Trp Val Phe Leu Val Phe Pro Ser Pro
 1               5                  10                  15

Gln

```
<210> SEQ ID NO 104
<211> LENGTH: 30
<212> TYPE: PRT
<213> ORGANISM: murine

<400> SEQUENCE: 104
```

Arg Arg Val Arg Gln Arg Thr Pro Asn Cys Arg Val Ile Ser Glu Phe
 1               5                  10                  15

Ser Met Gln Thr Ile Asp Asn Ala Cys Leu Cys Lys Cys Thr
            20                  25                  30

```
<210> SEQ ID NO 105
<211> LENGTH: 11
<212> TYPE: PRT
<213> ORGANISM: murine

<400> SEQUENCE: 105
```

Glu Leu Arg Ser Trp Leu Met Leu Lys Trp Asp
 1               5                  10

```
<210> SEQ ID NO 106
<211> LENGTH: 5
```

```
-continued

<212> TYPE: PRT
<213> ORGANISM: murine

<400> SEQUENCE: 106

Lys Lys Lys Lys Lys
  1               5
```

What is claimed is:

1. An isolated nucleic acid molecule encoding an envelope-interacting protein designated EIP-1 comprising consecutive amino acids having the sequence shown in SEQ ID NO:2.

2. The isolated nucleic acid molecule of claim 1, wherein the nucleic acid molecule is a DNA molecule.

3. The isolated DNA molecule of claim 2, wherein the DNA molecule is a cDNA molecule.

4. The isolated nucleic acid of claim 1, wherein the nucleic acid molecule is an RNA molecule.

5. The isolated nucleic acid molecule of claim 1, wherein the isolated nucleic acid molecule has the sequence shown in SEQ ID NO:1.

6. The isolated nucleic acid molecule of claim 1 operatively linked to a promoter of RNA transcription.

7. A vector comprising the nucleic acid molecule of claim 6.

8. The vector of claim 7 adapted for expression in a host cell which comprises the regulatory elements necessary for expression of the nucleic acid molecule in the host cell operatively linked to the nucleic acid molecule encoding the EIP-1 as to permit Depression of the EIP-1.

9. The vector of claim 8, wherein the host cell is a eukaryotic, bacterial, insect or yeast cell.

10. The vector of claim 9, wherein the eukaryotic host cell is a mammalian cell.

11. The vector of claim 10, wherein the vector is a plasmid.

12. The plasmid of claim 11 designated pCGN-EIP-1 (ATCC Designation No. 209885).

13. An isolated nucleic acid molecule encoding an envelope-interacting protein designated EIP-3 comprising consecutive amino acids having the sequence shown in SEQ ID NO:8.

14. The isolated nucleic acid molecule of claim 13, wherein the nucleic acid molecule is a DNA molecule.

15. The isolated DNA molecule of claim 14, wherein the DNA molecule is a cDNA molecule.

16. The isolated nucleic acid of claim 13, wherein the nucleic acid molecule is an RNA molecule.

17. The isolated nucleic acid molecule of claim 13, wherein the isolated nucleic acid molecule has the sequence shown in SEQ ID NO:5.

18. The isolated nucleic acid molecule of claim 17 operatively linked to a promoter of RNA transcription.

19. A vector comprising the nucleic acid molecule of claim 17.

20. The vector of claim 19 adapted for expression in a host cell which comprises the regulatory elements necessary for expression of the nucleic acid molecule in the host cell operatively linked to the nucleic acid molecule encoding the EIP-3 as to permit expression of the EIP-3.

21. The vector of claim 20, wherein the host cell is a eukaryotic, bacterial, insect or yeast cell.

22. The vector of claim 21, wherein the eukaryotic host cell is a mammalian cell.

23. The vector of claim 22, wherein the vector is a plasmid.

24. The plasmid of claim 23 designated pCGN-EIP-3 (ATCC Designation No. 209884).

* * * * *